(12) United States Patent
Kurihara et al.

(10) Patent No.: US 9,714,382 B2
(45) Date of Patent: *Jul. 25, 2017

(54) LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Eriko Kurihara, Chiba (JP); Masayuki Saito, Chiba (JP); Yoshimasa Furusato, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 4 days.

This patent is subject to a terminal disclaimer.

(21) Appl. No.: 14/825,162

(22) Filed: Aug. 12, 2015

(65) Prior Publication Data

US 2016/0090531 A1    Mar. 31, 2016

(30) Foreign Application Priority Data

Sep. 25, 2014  (JP) ................. 2014-194685

(51) Int. Cl.
| | | |
|---|---|---|
| *G02F 1/1333* | (2006.01) | |
| *C09K 19/34* | (2006.01) | |
| *C09K 19/30* | (2006.01) | |
| *C07C 43/225* | (2006.01) | |
| *C07D 309/06* | (2006.01) | |
| *C07D 311/60* | (2006.01) | |
| *C07C 57/62* | (2006.01) | |
| *C09K 19/54* | (2006.01) | |
| *C09K 19/04* | (2006.01) | |
| *C09K 19/12* | (2006.01) | |

(52) U.S. Cl.
CPC ........ *C09K 19/3402* (2013.01); *C07C 43/225* (2013.01); *C07C 57/62* (2013.01); *C07D 309/06* (2013.01); *C07D 311/60* (2013.01); *C09K 19/3048* (2013.01); *C09K 19/3066* (2013.01); *C09K 19/3068* (2013.01); *C09K 19/3098* (2013.01); *C09K 2019/0448* (2013.01); *C09K 2019/123* (2013.01); *C09K 2019/3004* (2013.01); *C09K 2019/3016* (2013.01); *C09K 2019/3021* (2013.01); *C09K 2019/3078* (2013.01); *C09K 2019/3422* (2013.01); *C09K 2019/3425* (2013.01); *C09K 2019/548* (2013.01)

(58) Field of Classification Search
CPC ............ C09K 19/3402; C09K 19/3066; C09K 19/3068; C09K 19/3048; C09K 19/3098; C09K 2019/3422; C09K 2019/3425; C09K 2019/3078; C09K 2019/548; C09K 2019/0448; C09K 2019/123; C09K 2019/3004; C09K 2019/3016; C09K 2019/3021; G02F 1/1333; C07C 43/225; C07C 57/62; C07D 309/06; C07D 311/60
USPC ............. 252/299.01, 299.6, 299.63; 349/183
See application file for complete search history.

(56) References Cited

U.S. PATENT DOCUMENTS

| | | | | |
|---|---|---|---|---|
| 8,398,887 B2 * | 3/2013 | Hu | ...................... | C09K 19/3048 252/299.63 |
| 8,580,146 B2 * | 11/2013 | Kobayashi | ......... | C09K 19/3048 252/299.01 |
| 2011/0260106 A1 | 10/2011 | Hu et al. | | |

FOREIGN PATENT DOCUMENTS

WO    2010139092    12/2010

* cited by examiner

*Primary Examiner* — Geraldina Visconti
(74) *Attorney, Agent, or Firm* — Jianq Chyun IP Office

(57) ABSTRACT

A liquid crystal composition having at least one or a suitable balance regarding at least two of characteristics such as high maximum temperature of a nematic phase, low minimum temperature thereof, small viscosity, suitable optical anisotropy, large negative dielectric anisotropy, large specific resistance, high stability to ultraviolet light or heat and a large elastic constant; an AM device having characteristics such as short response time, a large voltage holding ratio, low threshold voltage, a large contrast ratio and long service life are described. The liquid crystal composition has negative dielectric anisotropy, and contains a specific compound having negatively large dielectric anisotropy and a large elastic constant as a first component, and may contain a specific compound having high maximum temperature or small viscosity as a second component, a specific compound having negative dielectric anisotropy as a third component, and a specific compound having a polymerizable group as an additive component.

16 Claims, No Drawings

LIQUID CRYSTAL COMPOSITION AND LIQUID CRYSTAL DISPLAY DEVICE

CROSS-REFERENCE TO RELATED APPLICATION

This application claims the priority benefit of Japan application no. 2014-194685, filed on Sep. 25, 2014. The entirety of the above-mentioned patent application is hereby incorporated by reference herein and made a part of this specification.

TECHNICAL FIELD

The invention relates to a liquid crystal composition, a liquid crystal display device including the composition, and so forth. In particular, the invention relates to a liquid crystal composition having a negative dielectric anisotropy, and a liquid crystal display device including the composition and has a mode such as an in-plane switching (IPS) mode, a vertical alignment (VA) mode, a fringe field switching (FFS) mode and a field-induced photo-reactive alignment (FPA) mode. The invention also relates to a liquid crystal display device having a polymer sustained alignment mode.

BACKGROUND ART

In a liquid crystal display device, a classification based on an operating mode for liquid crystal molecules includes a phase change (PC) mode, a twisted nematic (TN) mode, a super twisted nematic (STN) mode, an electrically controlled birefringence (ECB) mode, an optically compensated bend (OCB) mode, an in-plane switching (IPS) mode, a vertical alignment (VA) mode, a fringe field switching (FFS) mode and a field induced photo-reactive alignment (FPA) mode. A classification based on a driving mode in the device includes a passive matrix (PM) and an active matrix (AM). The PM is classified into static, multiplex and so forth, and the AM is classified into a thin film transistor (TFT), a metal insulator metal (MIM) and so forth. The TFT is further classified into amorphous silicon and polycrystal silicon. The latter is classified into a high temperature type and a low temperature type according to a production process. A classification based on a light source includes a reflective type utilizing natural light, a transmissive type utilizing backlight and a transflective type utilizing both the natural light and the backlight.

A liquid crystal display device includes a liquid crystal composition having a nematic phase. The composition has suitable characteristics. An AM device having good characteristics can be obtained by improving the characteristics of the composition. Table 1 below summarizes a relationship of the characteristics between two aspects. The characteristics of the composition will be further described based on a commercially available AM device. A temperature range of the nematic phase relates to a temperature range in which the device can be used. A preferred maximum temperature of the nematic phase is approximately 70° C. or higher and a preferred minimum temperature of the nematic phase is approximately −10° C. or lower. Viscosity of the composition relates to a response time in the device. A short response time is preferred for displaying moving images on the device. A shorter response time even by one millisecond is desirable. Accordingly, a small viscosity in the composition is preferred. A small viscosity at a low temperature is further preferred.

TABLE 1

Characteristics of Composition and AM Device

| No. | Characteristics of Composition | Characteristics of AM Device |
|---|---|---|
| 1 | Wide temperature range of a nematic phase | Wide usable temperature range |
| 2 | Small viscosity | Short response time |
| 3 | Suitable optical anisotropy | Large contrast ratio |
| 4 | Large positive or negative dielectric anisotropy | Low threshold voltage and small electric power consumption Large contrast ratio |
| 5 | Large specific resistance | Large voltage holding ratio and large contrast ratio |
| 6 | High stability to ultraviolet light and heat | Long service life |
| 7 | Large elastic constant | Short response time and large contrast ratio |

An optical anisotropy of the composition relates to a contrast ratio in the device. According to the mode of the device, a suitable optical anisotropy such as a large optical anisotropy or a small optical anisotropy is required. A product ($\Delta n \times d$) of the optical anisotropy ($\Delta n$) of the composition and a cell gap (d) in the device is designed so as to maximize the contrast ratio. A suitable value of the product depends on a type of the operating mode. In a device having the VA mode, the suitable value is in the range of approximately 0.30 micrometer to approximately 0.40 micrometer, and in a device having the IPS mode or the FFS mode, the suitable value is in the range of approximately 0.20 micrometer to approximately 0.30 micrometer. In the above cases, a composition having a large optical anisotropy is preferred for a device having a small cell gap. A large value of dielectric anisotropy in the composition contributes to a low threshold voltage, a small electric power consumption and a large contrast ratio in the device. Accordingly, the large value of dielectric anisotropy is preferred. A large specific resistance in the composition contributes to a large voltage holding ratio and a large contrast ratio in the device. Accordingly, a composition having a large specific resistance at room temperature and also at a high temperature in an initial stage is preferred. A composition having a large specific resistance at room temperature and also at a high temperature even after the device has been used for a long period of time is preferred. Stability of the composition to ultraviolet light and heat relates to a service life of the device. In the case where the stability is high, the device has a long service life. Such characteristics are preferred for an AM device for use in a liquid crystal projector, a liquid crystal television and so forth.

A liquid crystal composition containing a polymer is used for a liquid crystal display device having the polymer sustained alignment (PSA) mode. First, a composition to which a small amount of polymerizable compound is added is injected into the device. Next, the composition is irradiated with ultraviolet light while voltage is applied between substrates of the device. The polymerizable compound is polymerized to form a network structure of the polymer in the composition. In the composition, alignment of liquid crystal molecules can be controlled by the polymer, and therefore a response time of the device is shortened and image persistence is improved. Such an effect of the polymer can be expected for a device having a mode such as the TN mode, the ECB mode, the OCB mode, the IPS mode, the VA mode, the FFS mode and the FPA mode.

A composition having a positive dielectric anisotropy is used for an AM device having the TN mode. A composition having a negative dielectric anisotropy is used for an AM device having the VA mode. A composition having a positive or negative dielectric anisotropy is used for an AM device having the IPS mode or the FFS mode. A composition having a positive or negative dielectric anisotropy is used for an AM device having the polymer sustained alignment mode. Examples of the compound related to the liquid crystal composition having the negative dielectric anisotropy are disclosed in Patent literature No. 1 as described below.

CITATION LIST

Patent Literature

Patent literature No. 1: WO 2010-139092 A.

SUMMARY OF INVENTION

Technical Problem

This invention provides a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light, a high stability to heat and a large elastic constant. This invention also provides a liquid crystal composition having a suitable balance regarding at least two of the characteristics. This invention further provides a liquid crystal display device including such a composition. This invention further provides an AM device having characteristics such as a short response time, a large voltage holding ratio, a low threshold voltage, a large contrast ratio and a long service life.

Solution to Problem

The invention concerns a liquid crystal composition having a negative dielectric anisotropy and contains at least one compound selected from the group of compounds represented by formula (1) as a first component, and a liquid crystal display device including the composition:

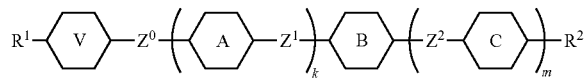
(1)

wherein, in formula (1), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine; ring V is 1,4-cyclohexylene or tetrahydropyran-2,5-diyl; ring A and ring C are independently 1,4-cyclohexylene, tetrahydropyran-2,5-diyl, 1,4-phenylene, or 1,4-phenylene in which at least one of hydrogen is replaced by fluorine or chlorine; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^0$, $Z^1$ and $Z^2$ are independently a single bond, ethylene, butene, carbonyloxy or methyleneoxy, wherein, at least one of $Z^0$, $Z^1$ and $Z^2$ is butene; k is 0, 1 or 2; m is 0 or 1; a sum of k and m is 2 or less.

The invention also concerns use of the liquid crystal composition in a liquid crystal display device.

The invention further concerns use of the liquid crystal composition in a polymer sustained alignment mode liquid crystal display device.

Advantageous Effects of Invention

An advantage of the invention is a liquid crystal composition satisfying at least one of characteristics such as a high maximum temperature of a nematic phase, a low minimum temperature of the nematic phase, a small viscosity, a suitable optical anisotropy, a large negative dielectric anisotropy, a large specific resistance, a high stability to ultraviolet light, a high stability to heat and a large elastic constant. Another advantage is a liquid crystal composition having a suitable balance regarding at least two of the characteristics. A further advantage is a liquid crystal display device including such a composition. An additional advantage is an AM device having characteristics such as a short response time, a large voltage holding ratio, a low threshold voltage, a large contrast ratio and a long service life.

DESCRIPTION OF EMBODIMENTS

Usage of terms herein is as described below. Terms "liquid crystal composition" and "liquid crystal display device" may be occasionally abbreviated as "composition" and "device," respectively. The liquid crystal display device is a generic term for a liquid crystal display panel and a liquid crystal display module. "Liquid crystal compound" is a generic term for a compound having a liquid crystal phase such as a nematic phase and a smectic phase, and a compound having no liquid crystal phase but being mixed with the composition for the purpose of adjusting characteristics such as a temperature range of the nematic phase, viscosity and dielectric anisotropy. The compound has a six-membered ring such as 1,4-cyclohexylene and 1,4-phenylene, and has rod like molecular structure. "Polymerizable compound" includes a compound to be added to the composition for the purpose of forming a polymer in the composition.

The liquid crystal composition is prepared by mixing a plurality of liquid crystal compounds. A ratio (content) of the liquid crystal compounds is expressed in terms of weight percent (% by weight) based on the weight of the liquid crystal composition. An additive such as an optically active compound, an antioxidant, an ultraviolet light absorber, a dye, an antifoaming agent, a polymerizable compound, a polymerization initiator and a polymerization inhibitor is added to the composition, when necessary. A ratio (amount of addition) of the additive is expressed in terms of weight percent (% by weight) based on the weight of the liquid crystal composition in a manner similar to the ratio of the liquid crystal compounds. Weight parts per million (ppm) may be occasionally used. A ratio of the polymerization initiator and the polymerization inhibitor is exceptionally expressed based on the weight of the polymerizable compound.

"Higher limit of the temperature range of the nematic phase" may be occasionally abbreviated as "maximum temperature." "A lower limit of the temperature range of the nematic phase" may be occasionally abbreviated as "minimum temperature." An expression "having a large specific resistance" means that the composition has a large specific resistance at room temperature and also at a temperature close to the maximum temperature of the nematic phase in an initial stage, and that the composition has a large specific resistance at room temperature and also at a temperature close to the maximum temperature of the nematic phase even after the device has been used for a long period of time. An expression "having a large voltage holding ratio" means that the device has a large voltage holding ratio at room temperature and also at a temperature close to the maximum temperature of the nematic phase in an initial stage, and that the device has a large voltage holding ratio at room temperature and also at a temperature close to the maximum temperature of the nematic phase even after the device has been used for a long period of time. An expression "increases the dielectric anisotropy" means that the value positively increases for the composition having a positive dielectric anisotropy, and means that the value negatively increases for the composition having a negative dielectric anisotropy.

A compound represented by formula (1) may be occasionally abbreviated as "compound (1)." At least one compound selected from the group of compounds represented by formula (3) may be occasionally abbreviated as "compound (3)." "Compound (3)" means one compound represented by formula (3), a mixture of two compounds represented thereby or a mixture of three or more compounds represented thereby. A same rule also applies to any other compound represented by any other formula. An expression "at least one of 'A'" means that the number of 'A' is arbitrary. An expression "at least one of 'A' may be replaced by 'B'" means that a position of 'A' is arbitrary when the number of 'A' is one, and that positions of 'A' can also be selected without limitation when the number of 'A' is two or more. A same rule also applies to an expression "at least one of 'A' is replaced by 'B'."

A symbol of terminal group R¹ is used for a plurality of compounds in chemical formula of component compounds. In the above compounds, two groups represented by two of arbitrary R¹ may be identical or different. For example, in one case, R¹ in compound (1-1) is ethyl and R in compound (1-2) is ethyl. In another case, R¹ of compound (1-1) is ethyl and R¹ of compound (1-2) is propyl. A same rule also applies to a symbol such as any other terminal group. In formula (3), when p is 2, two of ring F exists. In the compound, two rings represented by two of ring F may be identical or different. A same rule also applies to two of arbitrary ring D when n is larger than 2. A same rule also applies to a symbol such as Z¹ and ring I. A same rule also applies to such a case as two of -Sp²-P⁵ in compound (4-27).

A symbol such as A, B and C surrounded by a hexagonal shape correspond to a 6-membered ring or condensed ring, such as ring A, ring B and ring C, respectively. An oblique line crossing the hexagonal shape represents that arbitrary hydrogen on a ring may be replaced by a group such as -Sp¹-P¹. A subscript such as s represents the number of groups of being replaced. When the subscript is 0, no such replacement is made. When s is two or more, a plurality of -Sp¹-P¹ exist on ring J. The plurality of groups represented by -Sp¹-P¹ may be identical or different.

Then, 2-fluoro-1,4-phenylene means two divalent groups described below. In a chemical formula, fluorine may be leftward (L) or rightward (R). A same rule also applies to a ring having an asymmetrical divalent group, such as tetrahydropyran-2,5-diyl.

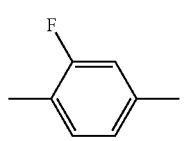

(L)

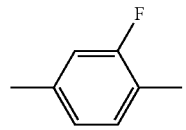

(R)

The invention includes items described below.

Item 1. A liquid crystal composition having a negative dielectric anisotropy and contains at least one compound selected from the group of compounds represented by formula (1) as a first component:

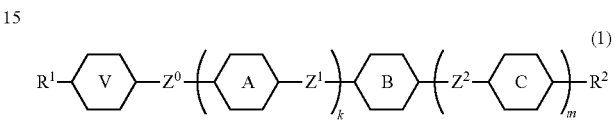

(1)

wherein, in formula (1), R¹ and R² are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine; ring V is 1,4-cyclohexylene or tetrahydropyran-2,5-diyl; ring A and ring C are independently 1,4-cyclohexylene, tetrahydropyran-2,5-diyl, 1,4-phenylene, or 1,4-phenylene in which at least one of hydrogen is replaced by fluorine or chlorine; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; Z⁰, Z¹ and Z² are independently a single bond, ethylene, butene, carbonyloxy or methyleneoxy, wherein, at least one of Z⁰, Z¹ and Z² is butene; k is 0, 1 or 2; m is 0 or 1; and a sum of k and m is 2 or less.

Item 2. The liquid crystal composition according to item 1, containing at least one compound selected from the group of compounds represented by formula (1-1) to formula (1-3) as the first component:

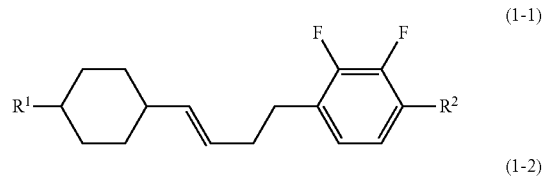

(1-1)

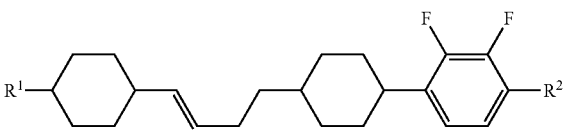

(1-2)

(1-3)

wherein, in formula (1-1) to formula (1-3), R¹ and R² are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine.

Item 3. The liquid crystal composition according to item 1 or 2, wherein a ratio of the first component is in the range of 3% by weight to 30% by weight based on the weight of the liquid crystal composition.

Item 4. The liquid crystal composition according to any one of items 1 to 3, containing at least one compound selected from the group of compounds represented by formula (2) as a second component:

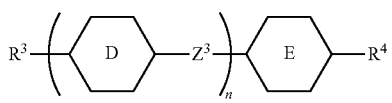
(2)

wherein, in formula (2), $R^3$ and $R^4$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine or chlorine, or alkenyl having 2 to 12 carbons in which at least one of hydrogen is replaced by fluorine or chlorine; ring D and ring E are independently 1,4-cyclohexylene, 1,4-phenylene, 2-fluoro-1,4-phenylene or 2,5-difluoro-1,4-phenylene; $Z^3$ is a single bond, ethylene or carbonyloxy; and n is 1, 2 or 3.

Item 5. The liquid crystal composition according to any one of items 1 to 4, containing at least one compound selected from the group of compounds represented by formula (2-1) to formula (2-13) as the second component:

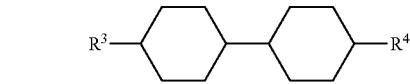
(2-1)

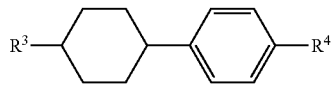
(2-2)

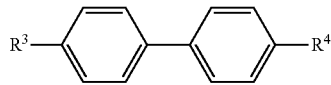
(2-3)

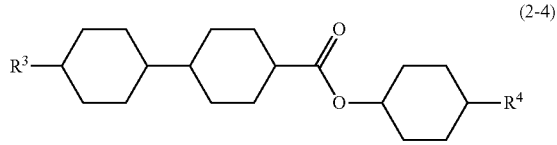
(2-4)

(2-5)

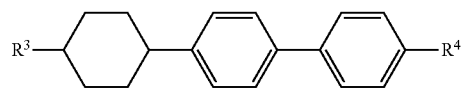
(2-6)

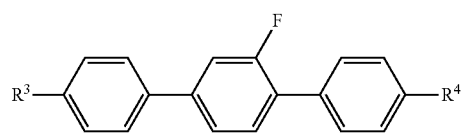
(2-7)

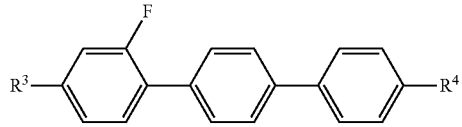
(2-8)

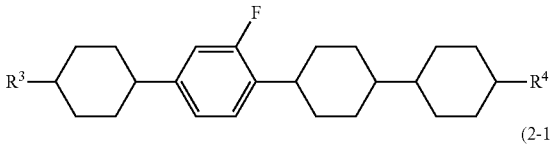
(2-9)

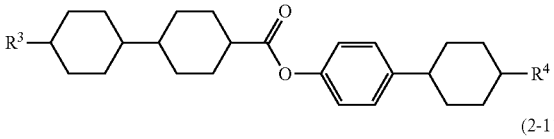
(2-10)

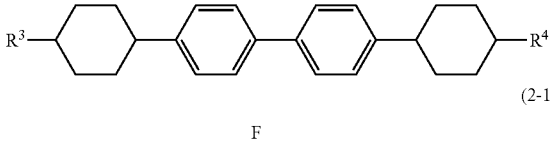
(2-11)

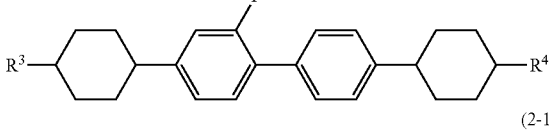
(2-12)

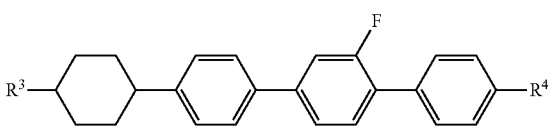
(2-13)

wherein, in formula (2-1) to formula (2-13), $R^3$ and $R^4$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine or chlorine, or alkenyl having 2 to 12 carbons in which at least one of hydrogen is replaced by fluorine or chlorine.

Item 6. The liquid crystal composition according to item 4 or 5, wherein a ratio of the second component is in the range of 20% by weight to 70% by weight based on the weight of the liquid crystal composition.

Item 7. The liquid crystal composition according to any one of items 1 to 6, containing at least one compound selected from the group of compounds represented by formula (3) as a third component:

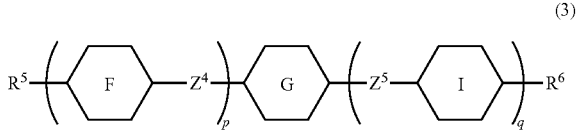
(3)

wherein, in formula (3), $R^5$ and $R^6$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine; ring F and ring I are independently 1,4-cyclohexylene, 1,4-cyclohexenylene, tetrahydropyran-2,5-diyl, 1,4-phenylene, or 1,4- phenylene in which at least one of hydrogen is replaced by fluorine or chlorine; ring G is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^4$ and $Z^5$ are independently a single bond, ethylene, carbonyloxy or methyleneoxy; p is 1, 2 or 3; q is 0 or 1; and a sum of p and q is 3 or less.

Item 8. The liquid crystal composition according to any one of items 1 to 7, containing at least one compound selected from the group of compounds represented by formula (3-1) to formula (3-19) as the third component:

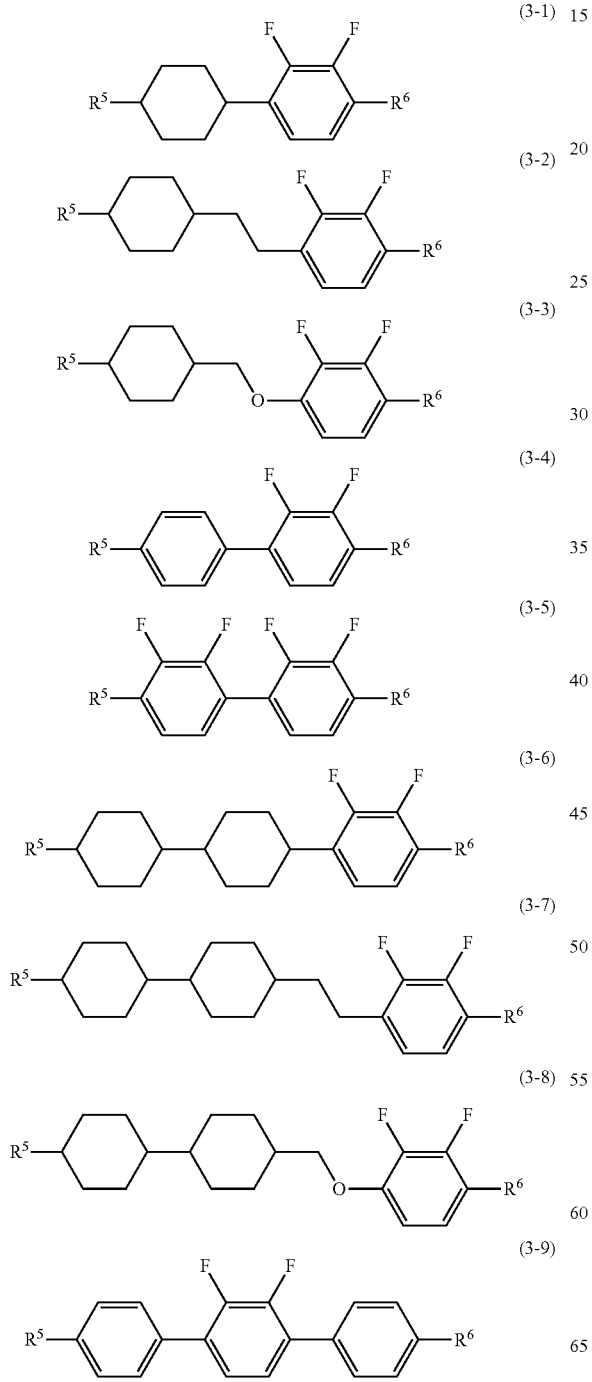

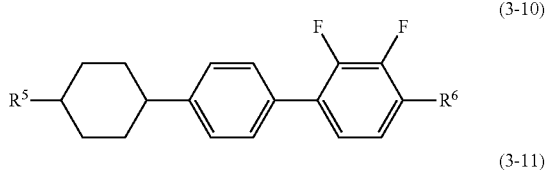

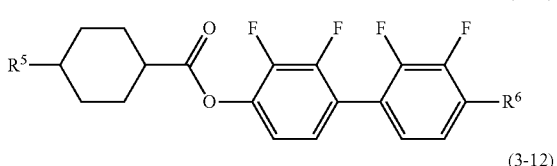

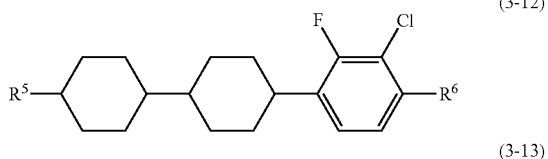

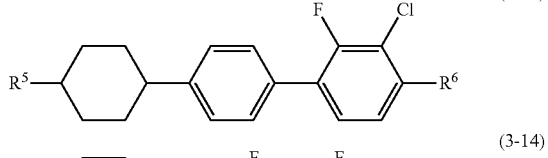

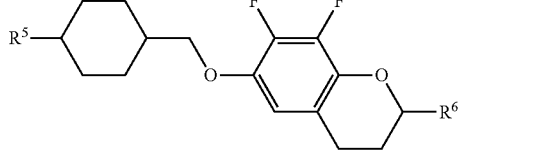

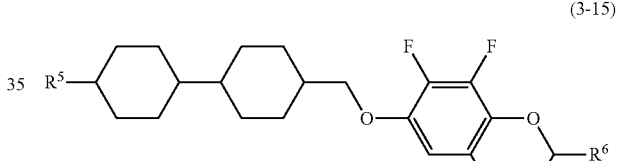

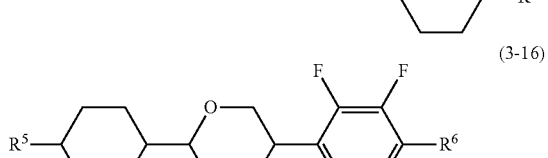

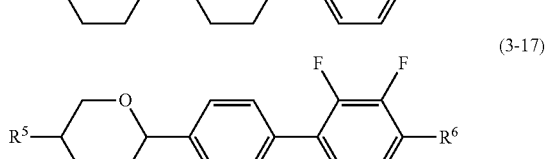

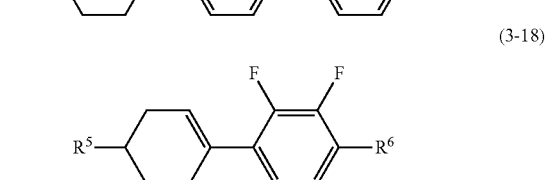

wherein, in formula (3-1) to formula (3-19), $R^5$ and $R^6$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine.

Item 9. The liquid crystal composition according to item 7 or 8, wherein a ratio of the third component is in the range of 20% by weight to 70% by weight based on the weight of the liquid crystal composition.

Item 10. The liquid crystal composition according to any one of items 1 to 9, containing at least one polymerizable compound selected from the group of compounds represented by formula (4) as an additive component:

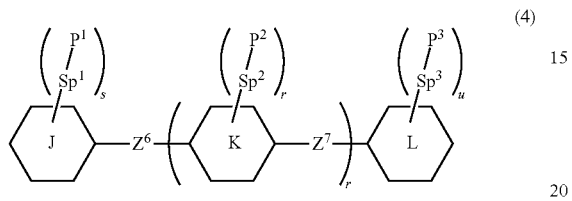

(4)

wherein, in formula (4), ring J and ring L are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by fluorine, chlorine, alkyl having 1 to 12 carbons, alkoxy having 1 to 12 carbons, or alkyl having 1 to 12 carbons in which at least one of hydrogen is replaced by fluorine or chlorine; ring K is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by fluorine, chlorine, alkyl having 1 to 12 carbons, alkoxy having 1 to 12 carbons, or alkyl having 1 to 12 carbons in which at least one of hydrogen is replaced by fluorine or chlorine; $Z^6$ and $Z^7$ are independently a single bond or alkylene having 1 to 10 carbons, in the alkylene, at least one of —CH$_2$— may be replaced by —O—, —CO—, —COO— or —OCO—, at least one of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, at least one of —CH$_2$—CH$_2$— may be replaced by —CH=CH— or —C≡C—, and in the groups, at least one of hydrogen may be replaced by fluorine or chlorine; r is 0, 1 or 2; s, t and u are independently 0, 1, 2, 3 or 4; and a sum of s, t and u is 1 or more.

Item 11. The liquid crystal composition according to item 10, wherein, in formula (4), $P^1$, $P^2$ and $P^3$ are independently a polymerizable selected from the group represented by formula (P-1) to formula (P-5):

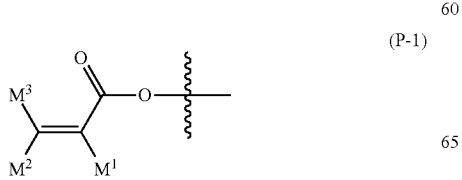

(P-1)

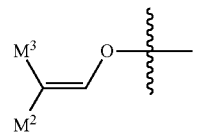

(P-2)

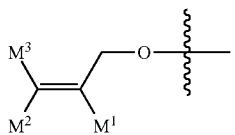

(P-3)

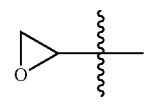

(P-4)

(P-5)

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one of hydrogen is replaced by fluorine or chlorine.

Item 12. The liquid crystal composition according to any one of items 1 to 11, containing at least one polymerizable compound selected from the group of compounds represented by formula (4-1) to formula (4-27) as the additive component:

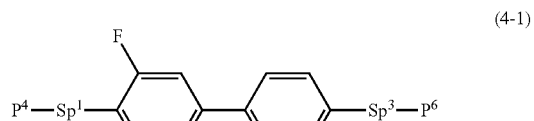

(4-1)

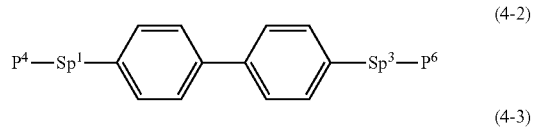

(4-2)

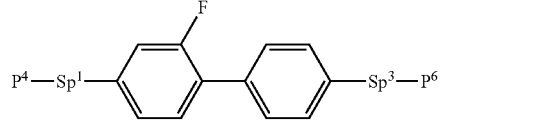

(4-3)

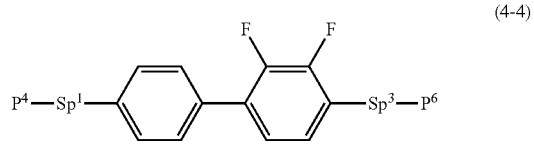

(4-4)

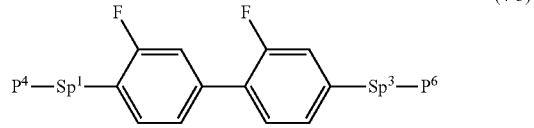

(4-5)

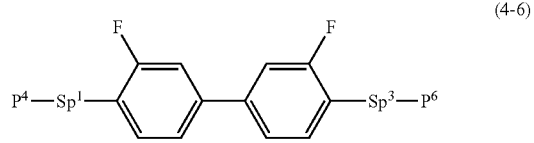

(4-6)

(4-7) 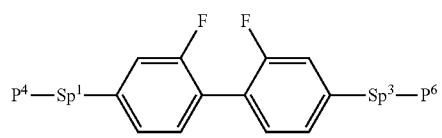
(4-8) 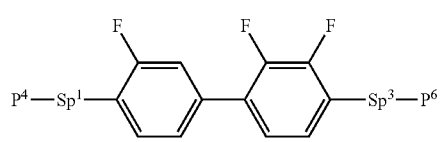
(4-9) 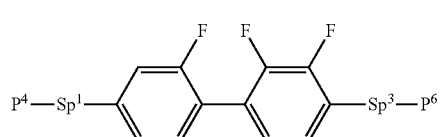
(4-10) 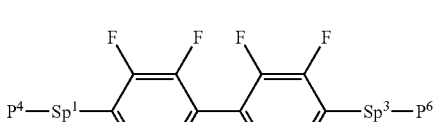
(4-11) 
(4-12) 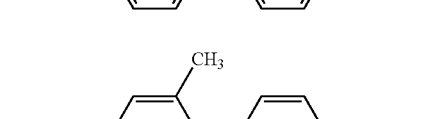
(4-13) 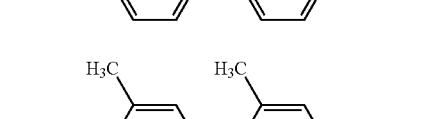
(4-14) 
(4-15) 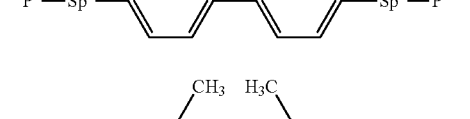
(4-16) 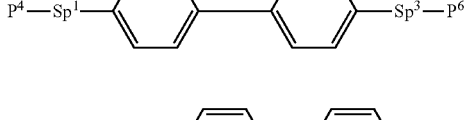
(4-17) 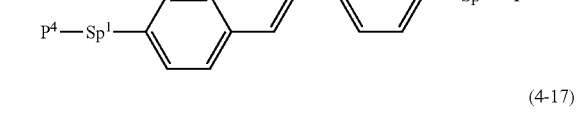
(4-18) 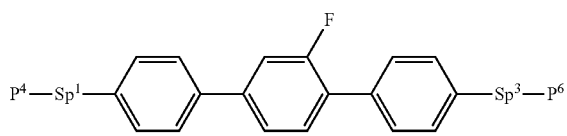
(4-19) 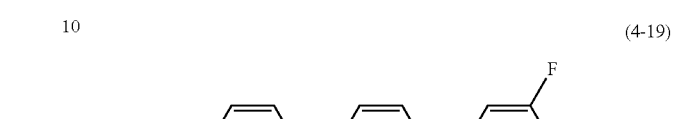
(4-20) 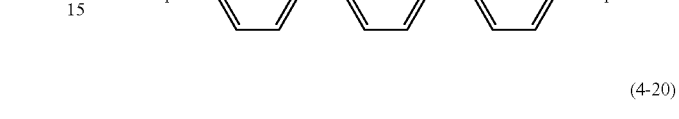
(4-21) 
(4-22) 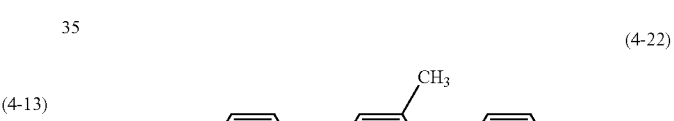
(4-23) 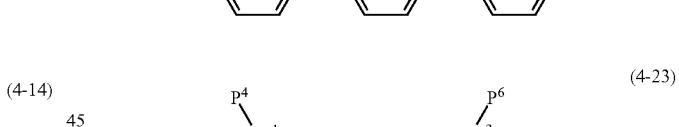
(4-24) 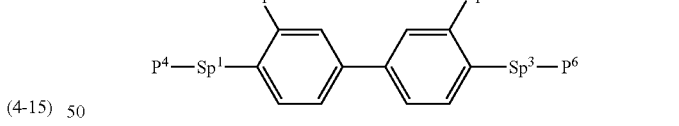
(4-25) 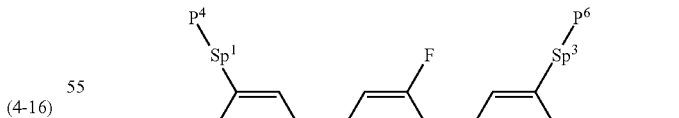

(4-26)

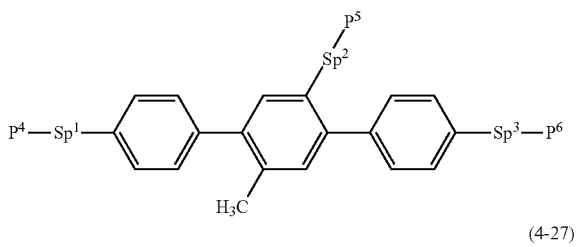

(4-27)

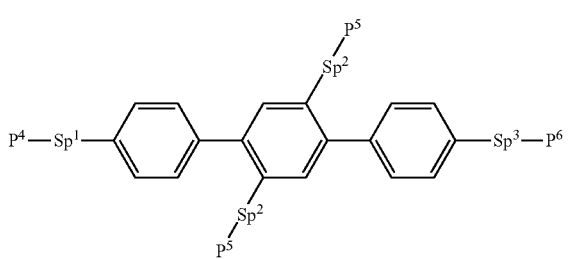

wherein, in formula (4-1) to formula (4-27), $P^4$, $P^5$ and $P^6$ are independently a polymerizable group selected from the group of groups represented by formula (P-1) to formula (P-3);

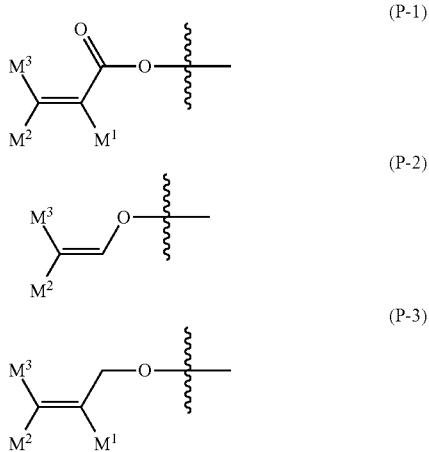

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by fluorine or chlorine; and
in formula (4-1) to formula (4-27), $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, at least one of —CH$_2$—CH$_2$— may be replaced by —CH=CH— or —C≡C—, and in the groups, at least one of hydrogen may be replaced by fluorine or chlorine.

Item 13. The liquid crystal composition according to any one of items 10 to 12, wherein a ratio of addition of the additive component is in the range of 0.03% by weight to 10% by weight based on the weight of the liquid crystal composition.

Item 14. A liquid crystal display device including the liquid crystal composition according to any one of items 1 to 13.

Item 15. The liquid crystal display device according to item 14, wherein an operating mode of the liquid crystal display is an IPS mode, a VA mode, an FFS mode or an FPA mode, and a driving mode of the liquid crystal display device is an active matrix mode.

Item 16. A polymer sustained alignment mode liquid crystal display device, wherein the device includes the liquid crystal composition according to any one of items 10 to 13, or a polymerizable compound in the liquid crystal composition is polymerized.

Item 17. Use of the liquid crystal composition according to any one of items 1 to 13 in a liquid crystal display device.

Item 18. Use of the liquid crystal composition according to any one of items 10 to 13 in a polymer sustained alignment mode liquid crystal display device.

The invention further includes the following items: (a) the composition, further containing at least one additive such as an optically active compound, an antioxidant, an ultraviolet light absorber, a dye, an antifoaming agent, a polymerizable compound, a polymerization initiator and a polymerization inhibitor; (b) an AM device including the composition; (c) a polymer sustained alignment (PSA) mode AM device, including the composition further containing a polymerizable compound; (d) a polymer sustained alignment (PSA) mode AM device, wherein the device includes the composition, and the polymerizable compound in the composition is polymerized; (e) a device including the composition and having the PC mode, the TN mode, the STN mode, the ECB mode, the OCB mode, the IPS mode, the VA mode, the FFS mode or the FPA mode; (f) a transmissive device including the composition; (g) use of the composition as the composition having the nematic phase; (h) use as an optically active composition by adding the optically active compound to the composition.

The composition of the invention will be described in the following order. First, a constitution of the component compounds in the composition will be described. Second, main characteristics of the component compounds and main effects of the compounds on the composition will be described. Third, a combination of components in the composition, a preferred ratio of the components and the basis thereof will be described. Fourth, a preferred embodiment of the component compounds will be described. Fifth, a preferred component compound will be shown. Sixth, an additive that may be added to the composition will be described. Seventh, methods for synthesizing the component compounds will be described. Last, an application of the composition will be described.

First, the constitution of the component compounds in the composition will be described. The composition of the invention is classified into composition A and composition B. Composition A may further contain any other liquid crystal compound, an additive or the like, in addition to the liquid crystal compound selected from compound (1), compound (2) and compound (3). "Any other liquid crystal compound" means a liquid crystal compound different from compound (1), compound (2) and compound (3). Such a compound is mixed with the composition for the purpose of further adjusting the characteristics. The additive includes the optically active compound, the antioxidant, the ultraviolet light absorber, the dye, the antifoaming agent, the polymerizable compound, the polymerization initiator and the polymerization inhibitor.

Composition B consists essentially of the liquid crystal compound selected from compound (1), compound (2) and compound (3). A term "essentially" means that the composition may contain the additive, but does not contain any other liquid crystal compound. Composition B has a smaller number of components than composition A has. Composition B is preferred to composition A in view of cost reduction. Composition A is preferred to composition B in view of possibility of further adjusting the characteristics by mixing any other liquid crystal compound.

Second, the main characteristics of the component compounds and the main effects of the compounds on the characteristics of the composition will be described. The main characteristics of the component compounds are summarized in Table 2 on the basis of advantageous effects of the invention. In Table 2, a symbol L stands for "large" or "high," a symbol M stands for "medium," and a symbol S stands for "small" or "low." The symbols L, M and S represent a classification based on qualitative comparison among the component compounds, and 0 (zero) means that the value is zero or nearly zero.

TABLE 2

Characteristics of Compounds

| Compounds | Compound (1) | Compound (2) | Compound (3) |
|---|---|---|---|
| Maximum temperature | S to L | S to L | S to L |
| Viscosity | M to L | S to M | M to L |
| Optical anisotropy | M to L | S to L | M to L |
| Dielectric anisotropy | L[1] | 0 | L[1] |
| Specific resistance | L | L | L |

[1]A value of dielectric anisotropy is negative.

Upon mixing the component compounds with the composition, the main effects of the component compounds on the characteristics of the composition are as described below. Compound (1) increases the dielectric anisotropy and increases the elastic constant. Compound (2) decreases the viscosity or increases the maximum temperature. Compound (3) increases the dielectric anisotropy and decreases the minimum temperature. Compound (4) gives a polymer by polymerization, and the polymer shortens the response time in the device, and improves image persistence.

Third, the combination of components in the composition, the preferred ratio of the component compound and the basis thereof will be described. The preferred combination of component in the composition includes a combination of the first component and the second component, a combination of the first component and the third component, a combination of the first component and the additive component, a combination of the first component, the second component and the third component, a combination of the first component, the second component and the additive component, a combination of the first component, the third component and the additive component, or a combination of the first component, the second component, the third component and the additive component. A further preferred combination includes the combination of the first component, the second component and the third component or a combination of the first component, the second component, the third component and the additive component.

A preferred ratio of the first component is approximately 3% by weight or more for increasing the dielectric anisotropy and approximately 30% by weight or less for decreasing the minimum temperature. A further preferred ratio is in the range of approximately 3% by weight to approximately 20% by weight based thereon. A particularly preferred ratio is in the range of approximately 3% by weight to approximately 15% by weight based thereon.

A preferred ratio of the second component is approximately 20% by weight or more for increasing the maximum temperature or decreasing the viscosity, and approximately 70% by weight or less for increasing the dielectric anisotropy. A further preferred ratio is in the range of approximately 20% by weight to approximately 65% by weight based thereon. A particularly preferred ratio is in the range of approximately 30% by weight to approximately 60% by weight based thereon.

A preferred ratio of the third component is approximately 20% by weight or more for increasing the dielectric anisotropy, and approximately 70% by weight or less for decreasing the minimum temperature. A further preferred ratio is in the range of approximately 25% by weight to approximately 65% by weight based thereon. A particularly preferred ratio is in the range of approximately 30% by weight to approximately 60% by weight based thereon.

Compound (4) is added for the purpose of adapting the composition for the polymer sustained alignment mode device. A preferred ratio of the additive component is approximately 0.03% by weight or more for aligning liquid crystal molecules, and approximately 10% by weight or less for preventing poor display on the device, based on the weight of the liquid crystal composition. A further preferred ratio of addition is in the range of approximately 0.1% by weight to approximately 2% by weight based thereon. A particularly preferred ratio of addition is in the range of approximately 0.2% by weight to approximately 1.0% by weight based thereon.

Fourth, the preferred embodiment of the component compounds will be described. In formula (1), formula (2) and formula (3), $R^3$ and $R^4$ are independently alkyl having 1 to 12 carbons, alkoxy having 1 to 12 carbons, alkenyl having 2 to 12 carbons, alkyl having 1 to 12 carbons in which at least one of hydrogen is replaced by fluorine or chlorine, or alkenyl having 2 to 12 carbons in which at least one of hydrogen is replaced by fluorine or chlorine. Preferred $R^3$ or $R^4$ is alkenyl having 2 to 12 carbons for decreasing the viscosity, and alkyl having 1 to 12 carbons for increasing the stability. $R^1$, $R^2$, $R^5$ and $R^6$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine. Preferred $R^1$, $R^2$, $R^5$ or $R^6$ is alkyl having 1 to 12 carbons for increasing the stability, and alkoxy having 1 to 12 carbons for increasing the dielectric anisotropy.

Preferred alkyl is methyl, ethyl, propyl, butyl, pentyl, hexyl, heptyl or octyl. Further preferred alkyl is ethyl, propyl, butyl, pentyl or heptyl for decreasing the viscosity.

Preferred alkoxy is methoxy, ethoxy, propoxy, butoxy, pentyloxy, hexyloxy or heptyloxy. Further preferred alkoxy is methoxy or ethoxy for decreasing the viscosity.

Preferred alkenyl is vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl or 5-hexenyl. Further preferred alkenyl is vinyl, 1-propenyl, 3-butenyl or 3-pentenyl for decreasing the viscosity. A preferred configuration of —CH═CH— in the alkenyl depends on a position of a double bond. Trans is preferred in alkenyl such as 1-propenyl, 1-butenyl, 1-pentenyl, 1-hexenyl, 3-pentenyl and 3-hexenyl for decreasing the viscosity, for instance. Cis is preferred in alkenyl such as 2-butenyl, 2-pentenyl and 2-hexenyl. In the alkenyl, straight-chain alkenyl is preferred to branched-chain alkenyl.

Preferred alkenyloxy is vinyloxy, allyloxy, 3-butenyloxy, 3-pentenyloxy or 4-pentenyloxy. Further preferred alkenyloxy is allyloxy or 3-butenyloxy for decreasing the viscosity.

Preferred examples of alkyl in which at least one of hydrogen is replaced by fluorine or chlorine include fluoromethyl, 2-fluoroethyl, 3-fluoropropyl, 4-fluorobutyl, 5-fluoropentyl, 6-fluorohexyl, 7-fluoroheptyl or 8-fluorooctyl. Further preferred examples include 2-fluoroethyl, 3-fluoropropyl, 4-fluorobuty or 5-fluoropentyl for increasing the dielectric anisotropy.

Preferred examples of alkenyl in which at least one of hydrogen is replaced by fluorine or chlorine include 2,2-difluorovinyl, 3,3-difluoro-2-propenyl, 4,4-difluoro-3-butenyl, 5,5-difluoro-4-pentenyl or 6,6-difluoro-5-hexenyl. Further preferred examples include 2,2-difluorovinyl or 4,4-difluoro-3-butenyl for decreasing the viscosity.

Ring V is 1,4-cyclohexylene or tetrahydropyran-2,5-diyl. Preferred ring V is 1,4-cyclohexylene for decreasing the viscosity, and tetrahydropyran-2,5-diyl for increasing the dielectric anisotropy. With regard to a configuration of 1,4-cyclohexylene, trans is preferred to cis for increasing the maximum temperature. Tetrahydropyran-2,5-diyl includes:

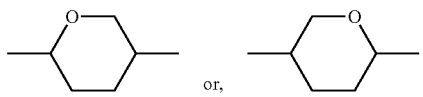

and preferably,

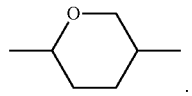

Ring A and ring C are independently 1,4-cyclohexylene, tetrahydropyran-2,5-diyl, 1,4-phenylene, or 1,4-phenylene in which at least one of hydrogen is replaced by fluorine or chlorine. Preferred examples of "1,4-phenylene in which at least one of hydrogen is replaced by fluorine or chlorine" include 2-fluoro-1,4-phenylene, 2,3-difluoro-1,4-phenylene or 2-chloro-3-fluoro-1,4-phenylene. Preferred ring A or ring C is 1,4-cyclohexylene for decreasing the viscosity, tetrahydropyran-2,5-diyl for increasing the dielectric anisotropy, and 1,4-phenylene for increasing the optical anisotropy.

Ring F and ring I are independently 1,4-cyclohexylene, 1,4-cyclohexenylene, tetrahydropyran-2,5-diyl, 1,4-phenylene, or 1,4-phenylene in which at least one of hydrogen is replaced by fluorine or chlorine. Preferred examples of "1,4-phenylene in which at least one of hydrogen is replaced by fluorine or chlorine" include 2-fluoro-1,4-phenylene, 2,3-difluoro-1,4-phenylene or 2-chloro-3-fluoro-1,4-phenylene. Preferred ring F or ring I is 1,4-cyclohexylene for decreasing the viscosity, tetrahydropyran-2,5-diyl for increasing the dielectric anisotropy, and 1,4-phenylene for increasing the optical anisotropy.

Ring B and ring G are independently 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl. Preferred ring B or ring G is 2,3-difluoro-1,4-phenylene for decreasing the viscosity, 2-chloro-3-fluoro-1,4-phenylene for decreasing the optical anisotropy, and 7,8-difluorochroman-2,6-diyl for increasing the dielectric anisotropy.

Ring D and ring E are independently 1,4-cyclohexylene, 1,4-phenylene, 2-fluoro-1,4-phenylene, or 2,5-difluoro-1,4-phenylene. Preferred ring D or ring E is 1,4-cyclohexylene for decreasing the viscosity or for increasing the maximum temperature, and 1,4-phenylene for decreasing the minimum temperature.

$Z^0$, $Z^1$ and $Z^2$ are independently a single bond, ethylene, butene, carbonyloxy or methyleneoxy, wherein, at least one of $Z^0$, $Z^1$ and $Z^2$ is butene. Preferred $Z^0$, $Z^1$ or $Z^2$ is a single bond for decreasing the viscosity, ethylene for decreasing the minimum temperature, butene for increasing the elastic constant, and methyleneoxy for increasing the dielectric anisotropy. $Z^3$ is a single bond, ethylene or carbonyloxy. Preferred $Z^3$ is a single bond for increasing the stability. $Z^4$ and $Z^5$ are independently a single bond, ethylene, carbonyloxy or methyleneoxy. Preferred $Z^4$ or $Z^5$ is a single bond for decreasing the viscosity, ethylene for decreasing the minimum temperature, and methyleneoxy for increasing the dielectric anisotropy.

Then, k is 0, 1 or 2, m is 0 or 1, and a sum of k and m is 2 or less. Preferred k is 0 for decreasing the viscosity, and 1 or 2 for increasing the maximum temperature. Preferred m is 0 for decreasing the viscosity, and 1 for decreasing the minimum temperature. Then n is 1, 2 or 3. Preferred n is 1 for decreasing the viscosity, and 2 or 3 for increasing the maximum temperature. Then, p is 1, 2 or 3, q is 0 or 1, and a sum of p and q is 3 or less. Preferred p is 1 for decreasing the viscosity, and 2 or 3 for increasing the maximum temperature. Preferred q is 0 for decreasing the viscosity, and 1 for decreasing the minimum temperature.

In formula (4), $P^1$, $P^2$ and $P^3$ are a polymerizable group. Preferred $P^1$, $P^2$ or $P^3$ is a polymerizable group selected from the group of groups represented by formula (P-1) to formula (P-5). Further preferred $P^1$, $P^2$ or $P^3$ is group (P-1) or group (P-2). Particularly preferred group (P-1) is —OCO—CH=CH$_2$ or —OCO—C(CH$_3$)=CH$_2$. A wavy line in group (P-1) to group (P-5) shows a site to be bonded.

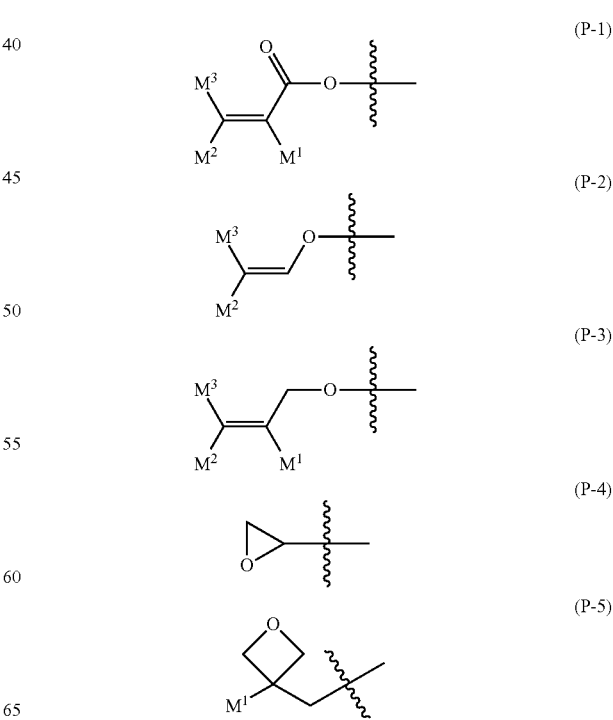

In group (P-1) to group (P-5), $M^1$, $M^2$ and $M^3$ are independently hydrogen, fluorine, alkyl having 1 to 5 carbons, or alkyl having 1 to 5 carbons in which at least one of hydrogen is replaced by fluorine or chlorine. Preferred $M^1$, $M^2$ or $M^3$ is hydrogen or methyl for increasing reactivity. Further preferred $M^1$ is methyl and further preferred $M^2$ or $M^3$ is hydrogen. When at least two of s pieces of $P^1$, t pieces of $P^2$, and u pieces of $P^3$ is group (P-1), two of arbitrary $M^1$, $M^2$ or $M^3$ of $P^1$, $P^2$ and $P^3$ may be identical or different. A same rule also applies to a case where the group is group (P-2) or group (P-3).

In formula (4-1) to formula (4-27), $P^4$, $P^5$ and $P^6$ are independently a group represented by formula (P-1) to formula (P-3). Preferred $P^4$, $P^5$ or $P^6$ is group (P-1) or group (P-2). Further preferred group (P-1) is —OCO—CH=$CH_2$ or —OCO—C($CH_3$)=$CH_2$. A wavy line in group (P-1) to group (P-3) shows a site to be bonded.

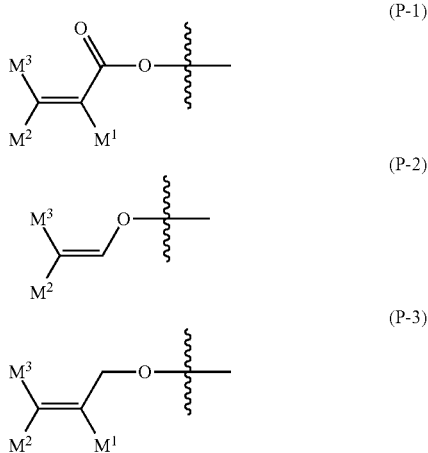

When at least two of one or two of $P^4$, one or two of $P^5$, and one or two of $P^6$ is group (P-1), two of arbitrary $M^1$, $M^2$ or $M^3$ among $P^4$, $P^5$ and $P^6$ may be identical or different. A same rule also applies to a case where the group is group (P-2) or group (P-3).

In formula (4), $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine. Preferred $Sp^1$, $Sp^2$ or $Sp^3$ is a single bond.

Ring J and ring L are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Preferred ring J or ring L is phenyl. Ring K is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by halogen, alkyl having 1 to 12 carbons, alkoxy having 1 to 12 carbons, or alkyl having 1 to 12 carbons in which at least one of hydrogen is replaced by halogen. Preferred ring K is 1,4-phenylene or 2-fluoro-1,4-phenylene.

$Z^6$ and $Z^7$ are independently a single bond or alkylene having 1 to 10 carbons, and in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine. Preferred $Z^6$ or $Z^7$ is a single bond, —$CH_2$—$CH_2$—, —$CH_2$O—, —$OCH_2$—, —COO— or —OCO—. Further preferred $Z^6$ or $Z^7$ is a single bond.

Then, r is 0, 1 or 2. Preferred r is 0 or 1. Then, s, t and u are independently 0, 1, 2, 3 or 4, and a sum of s, t and u is 1 or more. Preferred s, t or u is 1 or 2.

Fifth, the preferred component compound will be shown. Preferred compound (1) includes compound (1-1) to compound (1-3) as described in item 2. In the compounds, at least one of the first component is preferably compound (1-1) or (1-2).

Preferred compound (2) includes compound (2-1) to compound (2-13) as described in item 5. In the compounds, at least one of the second component is preferably compound (2-1), compound (2-3), compound (2-5), compound (2-6) or compound (2-7). At least two of the second components is preferably a combination of compound (2-1) and compound (2-3) and a combination of compound (2-1) and compound (2-5).

Preferred compound (3) includes compound (3-1) to compound (3-19) as described in item 8. In the compounds, at least one of the third component is preferably compound (3-1), compound (3-2), compound (3-3), compound (3-4), compound (3-6), compound (3-7), compound (3-8), compound (3-9) or compound (3-13). At least two of the third components is preferably a combination of compound (3-1) and compound (3-6), a combination of compound (3-1) and compound (3-13), a combination of compound (3-2) and compound (3-7), a combination of compound (3-3) and compound (3-6), a combination of compound (3-3) and compound (3-8), a combination of compound (3-4) and compound (3-6) or a combination of compound (3-4) and compound (3-8).

Preferred compound (4) includes compound (4-1) to compound (4-27) as described in item 12. In the compounds, at least one of the additive component is preferably compound (4-1), compound (4-2), compound (4-24), compound (4-25), compound (4-26) or compound (4-27). At least two of additive components is preferably a combination of compound (4-1) and compound (4-2), a combination of compound (4-1) and compound (4-18), a combination of compound (4-2) and compound (4-24), a combination of compound (4-2) and compound (4-25), a combination of compound (4-2) and compound (4-26), a combination of compound (4-25) and compound (4-26) or a combination of compound (4-18) and compound (4-24). In group (P-1) to group (P-3), preferred $M^1$, $M^2$ or $M^3$ is hydrogen or methyl. Preferred $Sp^1$, $Sp^2$ or $Sp^3$ is a single bond, —$CH_2$—$CH_2$—, —$CH_2$O—, —$OCH_2$—, —COO—, —OCO—, —CO—CH=CH— or —CH=CH—CO—.

Sixth, the additive that may be added to the composition will be described. Such an additive includes the optically active compound, the antioxidant, the ultraviolet light absorber, the dye, the antifoaming agent, the polymerizable compound, the polymerization initiator and the polymerization inhibitor. The optically active compound is added to the composition for the purpose of inducing a helical structure in the liquid crystal to give a twist angle. Examples of such a compound include compound (5-1) to compound (5-5). A preferred ratio of the optically active compound is approximately 5% by weight or less. A further preferred ratio is in the range of approximately 0.01% by weight to approximately 2% by weight.

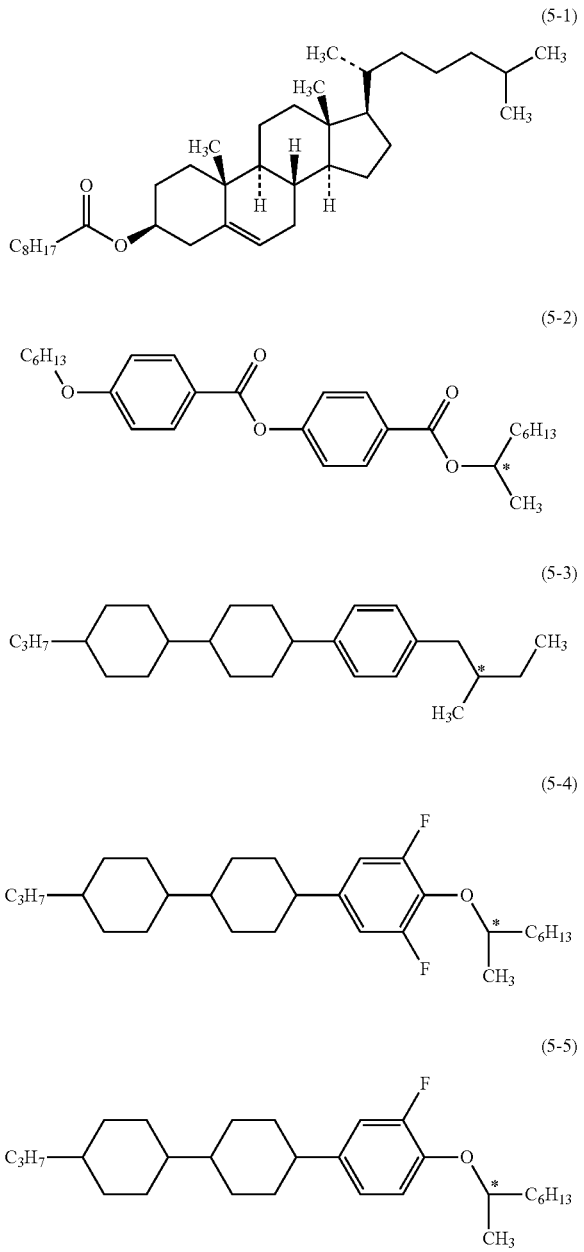

The antioxidant is added to the composition for the purpose of preventing a decrease in the specific resistance caused by heating in air, or maintaining a large voltage holding ratio at room temperature and also at a temperature close to the maximum temperature even after the device has been used for a long period of time. Preferred examples of the antioxidant include compound (6) where w is an integer of 1 to

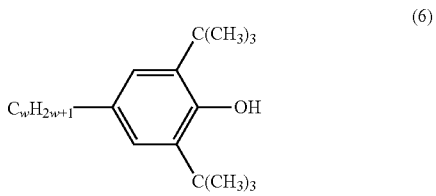

In compound (6), preferred w is 1, 3, 5, 7 or 9. Further preferred w is 7. Compound (6) is effective in maintaining a large voltage holding ratio at a room temperature and also at the temperature close to the maximum temperature even after the device has been used for a long period of time because compound (6) where w is 7 has a small volatility. A preferred ratio of the antioxidant is approximately 50 ppm or more for achieving the effect thereof, and approximately 600 ppm or less for avoiding a decrease in the maximum temperature or avoiding an increase in the minimum temperature. A further preferred ratio is in the range of approximately 100 ppm to approximately 300 ppm.

Preferred examples of the ultraviolet light absorber include a benzophenone derivative, a benzoate derivative and a triazole derivative. A light stabilizer such as an amine having steric hindrance is also preferred. A preferred ratio of the ultraviolet light absorber or the stabilizer is approximately 50 ppm or more for achieving the effect thereof, and approximately 10,000 ppm or less for avoiding a decrease in the maximum temperature or avoiding an increase in the minimum temperature. A further preferred ratio is in the range of approximately 100 ppm to approximately 10,000 ppm.

A dichroic dye such as an azo dye or an anthraquinone dye is added to the composition to be adapted for a device having a guest host (GH) mode. A preferred ratio of the dye is in the range of approximately 0.01% by weight to approximately 10% by weight. The antifoaming agent such as dimethyl silicone oil or methyl phenyl silicone oil is added to the composition for preventing foam formation. A preferred ratio of the antifoaming agent is approximately 1 ppm or more for achieving the effect thereof, and approximately 1,000 ppm or less for preventing poor display. A further preferred ratio is in the range of approximately 1 ppm to approximately 500 ppm.

The polymerizable compound is used to be adapted for the polymer sustained alignment (PSA) mode device. Compound (4) is suitable for the purpose. Any other polymerizable compound that is different from compound (4) may be added to the composition together with compound (4). Preferred examples of the polymerizable compounds include acrylate, methacrylate, a vinyl compound, a vinyloxy compound, propenyl ether, an epoxy compound (oxirane and oxetane) and vinyl ketone. Further preferred examples include an acrylate derivative or a methacrylate derivative. A preferred ratio of compound (4) is approximately 10% by weight or more based on the total weight of the polymerizable compound. A further preferred ratio is approximately 50% by weight or more based thereon. A particularly preferred ratio is approximately 80% by weight or more based thereon. A most preferred ratio is approximately 100% by weight based thereon.

The polymerizable compound such as compound (4) is polymerized by irradiation with ultraviolet light, and may be polymerized in the presence of a suitable initiator such as a photopolymerization initiator. Suitable conditions for polymerization, suitable types of the initiator and suitable amounts thereof are known to those skilled in the art and are described in literature. For example, Irgacure 651 (registered trademark; BASF), Irgacure 184 (registered trademark; BASF) or Darocur 1173 (registered trademark; BASF), each being a photoinitiator, is suitable for radical polymerization. A preferred ratio of the photopolymerization initiator is in the range of approximately 0.1% by weight to approximately 5% by weight based on the total weight of the polymerizable compound. A further preferred ratio is in the range of approximately 1% by weight to approximately 3% by weight based thereon.

When the polymerizable compound such as compound (4) is stored, the polymerization inhibitor may be added thereto for preventing polymerization. The polymerizable compound is ordinarily added to the composition without removing the polymerization inhibitor. Examples of the polymerization inhibitor include hydroquinone, a hydroquinone derivative such as methylhydroquinone, 4-tert-butylcatechol, 4-methoxyphenol and phenothiazine.

Seventh, the methods for synthesizing the component compounds will be described. The compounds can be prepared according to known methods. Examples of synthetic methods will be described. Compound (1-1) is prepared by the method described in WO 2010-139092 A. Compound (2-1) is prepared by the method described in JP S59-176221 A. Compound (3-6) is prepared by the method described in JP 2000-53602 A. Compound (4-18) is prepared by the method described in JP H7-101900 A. The oxidant inhibitor is commercially available. The compound where w is 1 in formula (6) can be obtained from Sigma-Aldrich Corporation. Compound (6) where w is 7 and so forth can be prepared according to the method described in U.S. Pat. No. 3,660,505 B.

Any compounds whose synthetic methods are not described above can be prepared according to the methods described in books such as Organic Syntheses (John Wiley & Sons, Inc.), Organic Reactions (John Wiley & Sons, Inc.), Comprehensive Organic Synthesis (Pergamon Press) and New Experimental Chemistry Course (Shin Jikken Kagaku Koza in Japanese) (Maruzen Co., Ltd.). The composition is prepared according to a publicly known method using the thus obtained compounds. For example, the component compounds are mixed and dissolved in each other by heating.

Last, the application of the composition will be described. The composition mainly has a minimum temperature of approximately −10° C. or lower, a maximum temperature of approximately 70° C. or higher, and the optical anisotropy in the range of approximately 0.07 to approximately 0.20. The device including the composition has a large voltage holding ratio. The composition is suitable for use in the AM device. The composition is particularly suitable for use in a transmissive AM device. The composition having an optical anisotropy in the range of approximately 0.08 to approximately 0.25 and further having an optical anisotropy in the range of approximately 0.10 to approximately 0.30 may be prepared by controlling the ratio of the component compounds or by mixing any other liquid crystal compound. The composition can be used as the composition having the nematic phase and as the optically active composition by adding the optically active compound.

The composition can be used for the AM device. The composition can also be used for a PM device. The composition can be used for an AM device and a PM device both having a mode such as PC, TN, STN, ECB, OCB, IPS, FFS, VA or FPA. Use for the AM device having the TN mode, the OCB mode, the IPS mode or the FFS mode is particularly preferred. In the AM device having the IPS mode or the FFS mode, alignment of liquid crystal molecules when no voltage is applied may be parallel or vertical to a glass substrate. The devices may be of a reflective type, a transmissive type or a transflective type. Use for the transmissive device is preferred. The composition can also be used for an amorphous silicon-TFT device or a polycrystal silicon-TFT device. The composition can also be used for a nematic curvilinear aligned phase (NCAP) device prepared by microencapsulating the composition, or for a polymer dispersed (PD) device in which a three-dimensional network-polymer is formed in the composition.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in more detail by way of Examples. The invention is not limited by the Examples. The invention includes a mixture of a composition in Example 1 and a composition in Example 2. The invention also includes a mixture in which at least two compositions in Examples were mixed. A compound synthesized was identified by a method such as an NMR analysis. Characteristics of the compound and the composition were measured by methods described below.

NMR analysis: For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane was used as an internal standard. In $^{19}$F-NMR measurement, measurement was carried out under conditions of 24 times of accumulation using $CFCl_3$ as an internal standard. In the explanation of nuclear magnetic resonance spectrum, s, d, t, q, quin, sex and m stand for a singlet, a doublet, a triplet, a quartet, a quintet, a sextet and a multiplet, respectively, and br means being broad.

Gas chromatographic analysis: GC-14B Gas Chromatograph made by Shimadzu Corporation was used for measurement. A carrier gas was helium (2 mL per minute). A sample injector and a detector (FID) were set to 280° C. and 300° C., respectively. A capillary column DB-1 (length 30 m, bore 0.32 mm, film thickness 0.25 μm; dimethylpolysiloxane as a stationary phase, non-polar) made by Agilent Technologies, Inc. was used for separation of component compounds. After a column was kept at 200° C. for 2 minutes, the column was heated to 280° C. at a rate of 5° C. per minute. A sample was prepared in an acetone solution (0.1% by weight), and then 1 microliter of the solution was injected into the sample injector. A recorder was C-R5A Chromatopac made by Shimadzu Corporation or the equivalent thereof. The resulting gas chromatogram showed a retention time of a peak and a peak area corresponding to each of the component compounds.

As a solvent for diluting the sample, chloroform, hexane or the like may also be used. The following capillary columns may also be used for separating the component compounds: HP-1 (length 30 m, bore 0.32 mm, film thickness 0.25 μm) made by Agilent Technologies, Inc., Rtx-1 (length 30 m, bore 0.32 mm, film thickness 0.25 μm) made by Restek Corporation and BP-1 (length 30 m, bore 0.32 mm, film thickness 0.25 μm) made by SGE International Pty. Ltd. A capillary column CBP1-M50-025 (length 50 m, bore 0.25 mm, film thickness 0.25 μm) made by Shimadzu Corporation may also be used for the purpose of avoiding an overlap of peaks of the compounds.

A ratio of liquid crystal compounds contained in the composition may be calculated by the method as described below. A mixture of the liquid crystal compounds was detected by gas chromatograph (FID). A ratio of the peak areas in the gas chromatogram corresponds to a ratio (weight ratio) of the liquid crystal compounds. When the capillary column described above was used, a correction coefficient of each of the liquid crystal compounds may be regarded as 1 (one). Accordingly, a ratio (% by weight) of the liquid crystal compounds can be calculated from the ratio of the peak areas.

Sample for measurement: When characteristics of the composition were measured, the composition was used as a sample as it was. When characteristics of the compound were measured, a sample for measurement was prepared by mixing the compound (15% by weight) with a base liquid crystal (85% by weight). Values of characteristics of the compound were calculated using values obtained by measurement, according to an extrapolation method: (extrapolated value)={(measured value of a sample for measurement)−0.85×(measured value of a base liquid crystal)}/0.15. When a smectic phase (or crystals) precipitated at the ratio thereof at 25° C., a ratio of the compound to the base liquid crystal was changed step by step in the order of (10% by weight: 90% by weight), (5% by weight: 95% by weight) and (1% by weight: 99% by weight). Values of maximum temperature, optical anisotropy, viscosity and dielectric anisotropy with regard to the compound were determined according to the extrapolation method.

The base liquid crystal described below was used. A ratio of the component compound was expressed in terms of weight percent (% by weight).

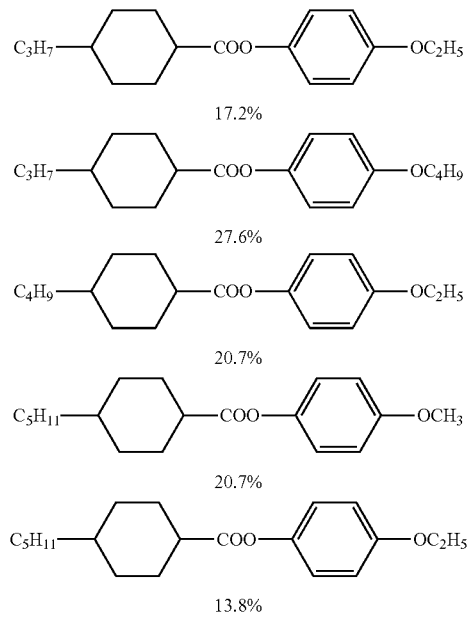

Measuring method: Characteristics were measured by methods described below. Most of the methods are applied as described in the Standard of Japan Electronics and Information Technology Industries Association (hereinafter, abbreviated as JEITA) discussed and established as the Standard of JEITA (JEITA ED-2521B), or as modified thereon. No thin film transistor (TFT) was attached to a TN device used for measurement.

(1) Maximum temperature of a nematic phase (NI; ° C.): A sample was placed on a hot plate in a melting point apparatus equipped with a polarizing microscope and was heated at a rate of 1° C. per minute. Temperature when part of the sample began to change from a nematic phase to an isotropic liquid was measured. A higher limit of a temperature range of the nematic phase may be occasionally abbreviated as "maximum temperature."

(2) Lower limit of a temperature of a nematic phase ($T_C$; ° C.): Samples each having a nematic phase were put in glass vials and kept in freezers at temperatures of 0° C., −10° C., −20° C., −30° C. and −40° C. for 10 days, and then liquid crystal phases were observed. For example, when the sample maintained the nematic phase at −20° C. and changed to crystals or a smectic phase at −30° C., $T_C$ was expressed as $T_C$<−20° C. A lower limit of the temperature range of the nematic phase may be occasionally abbreviated as "minimum temperature."

(3) Viscosity (bulk viscosity; η; measured at 20° C.; mPa·s): A cone-plate (E type) rotational viscometer made by Tokyo Keiki Inc. was used for measurement.

(4) Viscosity (rotational viscosity; γ1; measured at 25° C.; mPa·s): Measurement was carried out according to the method described in M. Imai et al., Molecular Crystals and Liquid Crystals, Vol. 259, p. 37 (1995). A sample was put in a VA device in which a distance (cell gap) between two glass substrates was 20 micrometers. Voltage was applied stepwise to the device in the range of 39 V to 50 V at an increment of 1 V. After 0.2 second with no voltage application, voltage was applied repeatedly under conditions of only one rectangular wave (rectangular pulse; 0.2 second) and no application (2 seconds). A peak current and a peak time of a transient current generated by the applied voltage were measured. A value of rotational viscosity was obtained from the measured values according to calculating equation (8) on page 40 of the paper presented by M. Imai et al. Dielectric anisotropy required for the calculation was measured by the method described in section (6).

(5) Optical anisotropy (refractive index anisotropy; Δn; measured at 25° C.): Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(6) Dielectric anisotropy (Δ∈; measured at 25° C.): A value of dielectric anisotropy was calculated from an equation: Δ∈=∈∥−∈⊥. A dielectric constant (∈∥ and ∈⊥) was measured as described below.

(6-1) Measurement of dielectric constant (∈∥): An ethanol (20 mL) solution of octadecyl triethoxysilane (0.16 mL) was applied to a well-cleaned glass substrate. After rotating the glass substrate with a spinner, the glass substrate was heated at 150° C. for 1 hour. A sample was put in a VA device in which a distance (cell gap) between two glass substrates was 4 micrometers, and the device was sealed with an ultraviolet-curable adhesive. Sine waves (0.5 V, 1 kHz) were applied to the device, and after 2 seconds, a dielectric constant (∈∥) in the major axis direction of liquid crystal molecules was measured.

(6-2) Measurement of dielectric constant (∈⊥): A polyimide solution was applied to a well-cleaned glass substrate. After calcining the glass substrate, rubbing treatment was applied to the alignment film obtained. A sample was put in a TN device in which a distance (cell gap) between two glass substrates was 9 micrometers and a twist angle was 80 degrees. Sine waves (0.5 V, 1 kHz) were applied to the device, and after 2 seconds, a dielectric constant (∈⊥) in the minor axis direction of the liquid crystal molecules was measured.

(7) Threshold voltage (Vth; measured at 25° C.; V): An LCD-5100 luminance meter made by Otsuka Electronics Co., Ltd. was used for measurement. A light source was a halogen lamp. A sample was put in a normally black mode VA device in which a distance (cell gap) between two glass substrates was 4 micrometers and a rubbing direction was anti-parallel, and the device was sealed with an ultraviolet-curable adhesive. A voltage (60 Hz, rectangular waves) to be applied to the device was stepwise increased from 0 V to 20 V at an increment of 0.02 V. On the occasion, the device was irradiated with light from a direction perpendicular to the device, and an amount of light transmitted through the device was measured. A voltage-transmittance curve was prepared, in which a maximum amount of light corresponds to 100% transmittance and a minimum amount of light corresponds to 0% transmittance. A threshold voltage is expressed in terms of a voltage at 10% transmittance.

(8) Voltage holding ratio (VHR-1; measured at 25° C.; %): A TN device used for measurement had a polyimide alignment film and a distance (cell gap) between two glass substrates was 5 micrometers. A sample was put in the device, and then the device was sealed with an ultraviolet-curable adhesive. A pulse voltage (60 microseconds at 5 V) was applied to the TN device and the device was charged. A decaying voltage was measured for 16.7 milliseconds with a high-speed voltmeter, and area A between a voltage curve and a horizontal axis in a unit cycle was determined. Area B was an area without decay. A voltage holding ratio is expressed in terms of a percentage of area A to area B.

(9) Voltage holding ratio (VHR-2; measured at 80° C.; %): A voltage holding ratio was measured in procedures identical with the procedures described above except that the voltage holding ratio was measured at 80° C. The values obtained were expressed by VHR-2.

(10) Voltage holding ratio (VHR-3; measured at 25° C.; %): Stability to ultraviolet light was evaluated by measuring a voltage holding ratio after a device was irradiated with ultraviolet light. A TN device used for measurement had a polyimide alignment film, and a cell gap was 5 micrometers. A sample was injected into the device, and then the device was irradiated with light for 20 minutes. A light source was an ultra high-pressure mercury lamp USH-500D (made by Ushio, Inc.), and a distance between the device and the light source was 20 centimeters. In measuring VHR-3, a decaying voltage was measured for 16.7 milliseconds. A composition having a large VHR-3 has a large stability to ultraviolet light. A value of VHR-3 is preferably 90% or more, and further preferably, 95% or more.

(11) Voltage holding ratio (VHR-4; measured at 25° C.; %): A TN device into which a sample was injected was heated in a constant-temperature bath at 80° C. for 500 hours, and then stability to heat was evaluated by measuring a voltage holding ratio. In measuring VHR-4, a decaying voltage was measured for 16.7 milliseconds. A composition having a large VHR-4 has a large stability to heat.

(12) Response time (τ; measured at 25° C.; ms): An LCD-5100 luminance meter made by Otsuka Electronics Co., Ltd. was used for measurement. A light source was a halogen lamp. A low-pass filter was set at 5 kHz. A sample was put in a normally black mode VA device in which a distance (cell gap) between two glass substrates was 4 micrometers and a rubbing direction was anti-parallel. Then, the device was sealed using an ultraviolet-curable adhesive. Rectangular waves (60 Hz, 10 V, 0.5 second) were applied to the device. On the occasion, the device was irradiated with light from a direction perpendicular to the device, and an amount of light transmitted through the device was measured. The maximum amount of light corresponds to 100% transmittance, and the minimum amount of light corresponds to 0% transmittance. A response time was expressed in terms of time required for a change from 90% transmittance to 10% transmittance (fall time; millisecond).

(13) Specific resistance (ρ; measured at 25° C.; Ωcm): Into a vessel equipped with electrodes, 1.0 milliliter of sample was injected. A DC voltage (10 V) was applied to the vessel, and a DC current after 10 seconds was measured. A specific resistance was calculated from the following equation: (specific resistance)={(voltage)×(electric capacity of a vessel)}/{(direct current)×(dielectric constant of vacuum)}.

(14) Elastic constant (K11: splay elastic constant, and K33: bend elastic constant; measured at 25° C.; pN): Elastic Constant Measurement System Model EC-1 made by TOYO Corporation was used for the measurement. A sample was put in a vertical alignment device in which a distance (cell gap) between two glass substrates was 20 micrometers. Voltage in the range of 0 V to 20 V was applied to the device, and electrostatic capacity and applied voltage were measured. Measured value of electrostatic-capacity (C) and the applied voltage (V) was fitted to equation (2.98) and equation (2.101) on page 75 of "Liquid Crystal Device Handbook (Ekisho Debaisu Handobukku in Japanese)" (Nikkan Kogyo Shimbun), and the value of elastic constant was obtained from equation (2.100).

The compounds in Examples were described using symbols according to definitions in Table 3 below. In Table 3, a configuration of 1,4-cyclohexylene is trans. A parenthesized number next to a symbolized compound corresponds to the number of the compound. A symbol (–) means any other liquid crystal compound. A ratio (percentage) of the liquid crystal compound is expressed in terms of weight percent (% by weight) based on the weight of the liquid crystal composition. Values of the characteristics of the composition were summarized in the last part.

TABLE 3

| Method for Description of Compounds using Symbols R—(A$_1$)—Z$_1$— - - - —Z$_n$—(A$_n$)—R' | |
|---|---|
|  | Symbol |
| 1) Left-terminal Group R— | |
| $C_nH_{2n+1}$— | n- |
| $C_nH_{2n+1}O$— | nO- |
| $C_mH_{2m+1}OC_nH_{2n}$— | mOn- |
| $CH_2$=CH— | V- |
| $C_nH_{2n+1}$—CH=CH— | nV- |
| $CH_2$=CH—$C_nH_{2n}$— | Vn- |
| $C_mH_{2m+1}$—CH=CH—$C_nH_{2n}$— | mVn- |

TABLE 3-continued

Method for Description of Compounds using Symbols
R—(A₁)—Z₁— - - - —Zₙ—(Aₙ)—R'

| | Symbol |
|---|---|
| CF₂=CH— | VFF- |
| CF₂=CH—CₙH₂ₙ— | VFFn- |
| CH₂=CH—COO— | AC- |
| F—CₙH₂ₙ— | Fn- |
| CH₂=C(CH₃)—COO— | MAC- |
| 2) Right-terminal Group —R' | |
| —CₙH₂ₙ₊₁ | -n |
| —OCₙH₂ₙ₊₁ | -On |
| —CH=CH₂ | -V |
| —CH=CH—CₙH₂ₙ₊₁ | -Vn |
| —CₙH₂ₙ—CH=CH₂ | -nV |
| —CₘH₂ₘ—CH=CH—CₙH₂ₙ₊₁ | -mVn |
| —CH=CF₂ | -VFF |
| —OCO—CH=CH₂ | -AC |
| —OCO—C(CH₃)=CH₂ | -MAC |
| 3) Bonding Group —Zₙ— | |
| —CₙH₂ₙ— | n |
| —COO— | E |
| —CH=CH— | V |
| —CH=CHC₂H₄— | V2 |
| —C₂H₄CH=CH— | 2V |
| —CH₂O— | 1O |
| —OCH₂— | O1 |
| 4) Ring Structure —Aₙ— | |

| | Symbol |
|---|---|
|  | H |
|  | B |
| 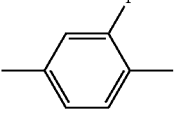 | B(F) |
| 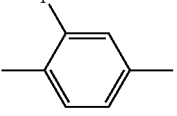 | B(2F) |
| 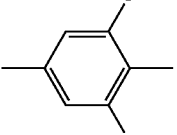 | B(F,F) |
| 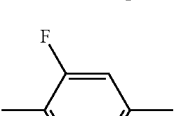 | B(2F,5F) |
| 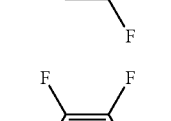 | B(2F,3F) |

TABLE 3-continued

Method for Description of Compounds using Symbols
R—(A₁)—Z₁— - - - —Zₙ—(Aₙ)—R'

| | Symbol |
|---|---|
| 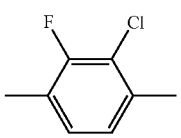 | B(2F,3CL) |
| 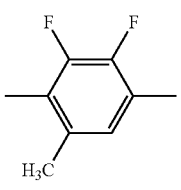 | B(2F,3F,6Me) |
| 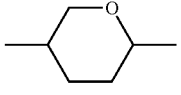 | dh |
| 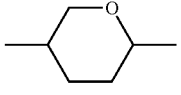 | Dh |
| 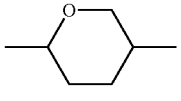 | ch |
| 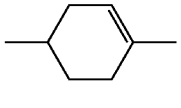 | Cro(7F,8F) |

5) Examples of Description

Example 1 3-HV2B(2F,3F)-O2

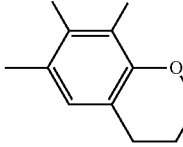

Example 2 3-HHB(2F,3F)-O2

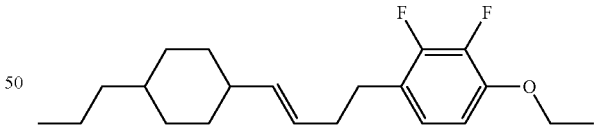

Example 3 V-HBB-1

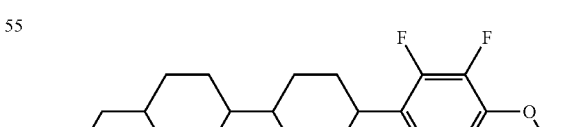

TABLE 3-continued

Method for Description of Compounds using Symbols
R—(A₁)—Z₁— - - - —Zₙ—(Aₙ)—R'

Symbol

Example 4  3-HDhB(2F,3F)-O2

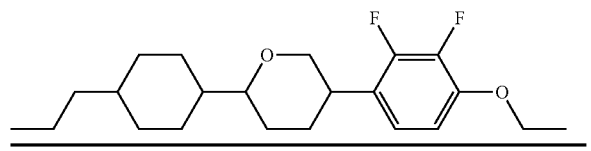

Example 1

| | | |
|---|---|---|
| 3-HV2HB(2F,3F)-O2 | (1-2) | 8% |
| 2-HH-3 | (2-1) | 20% |
| 3-HH-4 | (2-1) | 6% |
| 1-BB-3 | (2-3) | 7% |
| 3-HHB-O1 | (2-5) | 3% |
| 3-HHB-1 | (2-5) | 3% |
| 3-HHB-3 | (2-5) | 3% |
| 3-BB(2F,3F)-O2 | (3-4) | 12% |
| 5-BB(2F,3F)-O2 | (3-4) | 8% |
| 2-HH1OB(2F,3F)-O2 | (3-8) | 10% |
| 3-HH1OB(2F,3F)-O2 | (3-8) | 20% |

NI=75.5° C.; Tc<−20° C.; Δn=0.099; Δ∈=−3.8; Vth=2.11 V; η=21.1 mPa·s; K33=14.6 pN.

Comparative Example 1

The composition in Example 1 contains compound (1) being a first component. Compound (1) has negative dielectric anisotropy. For comparison, a composition prepared by replacing the compound being the first component in Example 1 by a similar compound was taken as Comparative Example 1.

| | | |
|---|---|---|
| 3-H4HB(2F,3F)-O2 | (—) | 3% |
| 3-H4HB(2F,3F)-O4 | (—) | 5% |
| 2-HH-3 | (2-1) | 20% |
| 3-HH-4 | (2-1) | 6% |
| 1-BB-3 | (2-3) | 7% |
| 3-HHB-O1 | (2-5) | 3% |
| 3-HHB-1 | (2-5) | 3% |
| 3-HHB-3 | (2-5) | 3% |
| 3-BB(2F,3F)-O2 | (3-4) | 12% |
| 5-BB(2F,3F)-O2 | (3-4) | 8% |
| 2-HH1OB(2F,3F)-O2 | (3-8) | 10% |
| 3-HH1OB(2F,3F)-O2 | (3-8) | 20% |

NI=75.3° C.; Tc>20° C. (Crystal precipitated at 20° C.); Δn=0.098; Δ∈=−3.6; Vth=2.15 V.

Example 2

| | | |
|---|---|---|
| V-HV2HB(2F,3F)-O2 | (1-2) | 7% |
| 3-HH-V | (2-1) | 16% |
| 4-HH-V1 | (2-1) | 9% |
| 1V2-BB-1 | (2-3) | 4% |
| V-HHB-1 | (2-5) | 8% |
| V2-HHB-1 | (2-5) | 5% |
| V-HBB-2 | (2-6) | 5% |
| V-HB(2F,3F)-O2 | (3-1) | 4% |
| 3-HB(2F,3F)-O2 | (3-1) | 6% |
| 3-H1OB(2F,3F)-O2 | (3-3) | 5% |
| 3-BB(2F,3F)-O2 | (3-4) | 8% |
| 5-B(2F,3F)B(2F,3F)-O2 | (3-5) | 4% |
| 2-HH1OB(2F,3F)-O2 | (3-8) | 5% |
| 3-HH1OB(2F,3F)-O2 | (3-8) | 14% |

NI=73.8° C.; Tc<−20° C.; Δn=0.100; Δ∈=−3.5; Vth=2.20 V; η=16.8 mPa·s.

Example 3

| | | |
|---|---|---|
| V-HV2B(2F,3F)-O2 | (1-1) | 3% |
| V-HV2HB(2F,3F)-O2 | (1-2) | 3% |
| 3-HH-V | (2-1) | 11% |
| 1V2-HH-3 | (2-1) | 5% |
| 2-HH-3 | (2-1) | 12% |
| 3-HB-O2 | (2-2) | 5% |
| 3-HHEH-3 | (2-4) | 4% |
| 3-HHEH-5 | (2-4) | 4% |
| V-HHB-1 | (2-5) | 5% |
| 3-H2B(2F,3F)-O2 | (3-2) | 4% |
| 5-H2B(2F,3F)-O2 | (3-2) | 4% |
| 3-BB(2F,3F)-O2 | (3-4) | 4% |
| 5-BB(2F,3F)-O2 | (3-4) | 4% |
| 2-HH1OB(2F,3F)-O2 | (3-8) | 5% |
| 3-HH1OB(2F,3F)-O2 | (3-8) | 14% |
| 3-H1OCro(7F,8F)-5 | (3-14) | 5% |
| 3-HH1OCro(7F,8F)-5 | (3-15) | 8% |

NI=73.0° C.; Tc<−20° C.; Δn=0.080; Δ∈=−4.2; Vth=1.96 V; η=24.0 mPa·s.

Example 4

| | | |
|---|---|---|
| V-HV2BB(2F,3F)-O4 | (1-3) | 8% |
| 3-HH-V | (2-1) | 18% |
| 1V2-HH-1 | (2-1) | 3% |
| 2-HH-3 | (2-1) | 6% |
| VFF2-HHB-1 | (2-5) | 3% |
| 3-HBB-2 | (2-6) | 4% |
| 5-B(F)BB-2 | (2-8) | 4% |
| 5-HBB(F)B-2 | (2-13) | 3% |
| V-HB(2F,3F)-O2 | (3-1) | 4% |
| 3-BB(2F,3F)-O2 | (3-4) | 11% |
| 5-BB(2F,3F)-O2 | (3-4) | 6% |
| V2-HHB(2F,3F)-O2 | (3-6) | 7% |
| 2-HH1OB(2F,3F)-O2 | (3-8) | 5% |
| 3-HH1OB(2F,3F)-O2 | (3-8) | 6% |
| 3-HBB(2F,3CL)-O2 | (3-13) | 4% |
| 3-dhBB(2F,3F)-O2 | (3-17) | 5% |
| 1O1-HBBH-5 | (—) | 3% |

NI=87.7° C.; Tc<−20° C.; Δn=0.124; Δ∈=−3.4; Vth=2.25 V; η=22.6 mPa·s.

Example 5

| | | |
|---|---|---|
| V-HV2BB(2F,3F)-O2 | (1-3) | 5% |
| V-HHV2B(2F,3F)-O2 | (1) | 4% |
| 3-HH-V | (2-1) | 18% |
| 3-HH-V1 | (2-1) | 7% |
| 5-HH-V | (2-1) | 6% |
| V2-BB-1 | (2-3) | 5% |
| 2-BB(F)B-3 | (2-7) | 4% |

-continued

| | | |
|---|---|---|
| 3-HB(F)HH-2 | (2-9) | 4% |
| 3-H1OB(2F,3F)-O2 | (3-3) | 9% |
| 3-HHB(2F,3F)-O2 | (3-6) | 6% |
| 3-HH2B(2F,3F)-O2 | (3-7) | 7% |
| 3-HH1OB(2F,3F)-O2 | (3-8) | 9% |
| 2-BB(2F,3F)B-4 | (3-9) | 4% |
| V-HBB(2F,3F)-O2 | (3-10) | 6% |
| 3-HHB(2F,3CL)-O2 | (3-12) | 6% |

NI=94.7° C.; Tc<−20° C.; Δn=0.113; Δ∈=−3.4; Vth=2.16 V; η=18.0 mPa·s.

Example 6

| | | |
|---|---|---|
| 3-HV2B(2F,3F)-O2 | (1-1) | 4% |
| V-HV2HB(2F,3F)-O4 | (1-2) | 4% |
| V-HHV2B(2F,3F)-O2 | (1) | 3% |
| 3-HH-V | (2-1) | 16% |
| 3-HH-V1 | (2-1) | 7% |
| 3-HH-4 | (2-1) | 7% |
| 1-BB-3 | (2-3) | 8% |
| 3-HHB-1 | (2-5) | 3% |
| 3-HHB-3 | (2-5) | 3% |
| 1-BB(F)B-2V | (2-7) | 3% |
| 2-BB(F)B-2V | (2-7) | 3% |
| 3-HHEBH-5 | (2-10) | 3% |
| 3-H1OB(2F,3F)-O2 | (3-3) | 7% |
| 5-B(2F,3F)B(2F,3F)-O2 | (3-5) | 3% |
| V-HHB(2F,3F)-O2 | (3-6) | 8% |
| 3-HBB(2F,3F)-O2 | (3-10) | 5% |
| 5-HHB(2F,3CL)-O2 | (3-12) | 4% |
| 5-HBB(2F,3CL)-O2 | (3-13) | 4% |
| 3-HDhB(2F,3F)-O2 | (3-16) | 5% |

NI=85.0° C.; Tc<−20° C.; Δn=0.107; Δ∈=−2.8; Vth=2.30 V; η=19.4 mPa·s.

Example 7

| | | |
|---|---|---|
| 3-HV2HB(2F,3F)-O2 | (1-2) | 9% |
| 3-HH-V | (2-1) | 15% |
| 4-HH-V | (2-1) | 10% |
| F3-HH-V1 | (2-1) | 3% |
| V-HHB-1 | (2-5) | 5% |
| V2-HHB-1 | (2-5) | 5% |
| 5-BB(2F,3F)-O2 | (3-4) | 8% |
| 2-HH1OB(2F,3F)-O2 | (3-8) | 10% |
| 3-HH1OB(2F,3F)-O2 | (3-8) | 19% |
| 2-BB(2F,3F)B-3 | (3-9) | 9% |
| 2-BB(2F,3F)B-4 | (3-9) | 7% |

NI=92.9° C.; Tc<−20° C.; Δn=0.114; Δ∈=−3.6; Vth=2.10 V; η=21.9 mPa·s.

Example 8

| | | |
|---|---|---|
| V-HV2B(2F,3F)-O2 | (1-1) | 4% |
| V-HV2HB(2F,3F)-O2 | (1-2) | 4% |
| 3-HH-V | (2-1) | 20% |
| 3-HH-V1 | (2-1) | 10% |
| V-HHB-1 | (2-5) | 8% |
| 5-HBBH-3 | (2-11) | 3% |
| 5-HB(F)BH-3 | (2-12) | 4% |
| 3-BB(2F,3F)-O2 | (3-4) | 11% |
| V2-BB(2F,3F)-O2 | (3-4) | 5% |
| 2-HH1OB(2F,3F)-O2 | (3-8) | 7% |
| 3-HH1OB(2F,3F)-O2 | (3-8) | 10% |
| 3-H1OCro(7F,8F)-5 | (3-14) | 6% |
| 3-chB(2F,3F)-O2 | (3-18) | 8% |

NI=71.9° C.; Tc<−20° C.; Δn=0.099; Δ∈=−3.8; Vth=2.12 V; η=20.2 mPa·s.

Example 9

| | | |
|---|---|---|
| 3-HV2B(2F,3F)-O2 | (1-1) | 3% |
| V-HV2HB(2F,3F)-O1 | (1-2) | 3% |
| 3-HH-VFF | (2-1) | 4% |
| 2-HH-3 | (2-1) | 20% |
| 3-HH-4 | (2-1) | 5% |
| 1-BB-5 | (2-3) | 4% |
| VFF-HHB-1 | (2-5) | 3% |
| V-HHB-1 | (2-5) | 4% |
| V2-HHB-1 | (2-5) | 3% |
| 2-BB(F)B-2V | (2-7) | 3% |
| 3-BB(2F,3F)-O2 | (3-4) | 6% |
| 3-HHB(2F,3F)-O2 | (3-6) | 5% |
| V-HHB(2F,3F)-O2 | (3-6) | 5% |
| 3-HH2B(2F,3F)-O2 | (3-7) | 3% |
| 3-HH1OB(2F,3F)-O2 | (3-8) | 14% |
| 3-HDhB(2F,3F)-O2 | (3-16) | 7% |
| 3-HchB(2F,3F)-O2 | (3-19) | 8% |

NI=92.3° C.; Tc<−20° C.; Δn=0.097; Δ∈=−3.3; Vth=2.19 V; η=19.8 mPa·s.

Example 10

| | | |
|---|---|---|
| V-HV2BB(2F,3F)-O2 | (1-3) | 8% |
| 3-HH-V | (2-1) | 20% |
| 3-HH-V1 | (2-1) | 11% |
| F3-HH-V | (2-1) | 4% |
| 1V2-BB-1 | (2-3) | 4% |
| V-HBB-3 | (2-6) | 3% |
| 2-BB(F)B-5 | (2-7) | 4% |
| 5-B(F)BB-3 | (2-8) | 3% |
| 3-BB(2F,3F)-O2 | (3-4) | 10% |
| 5-BB(2F,3F)-O2 | (3-4) | 7% |
| 2-HH1OB(2F,3F)-O2 | (3-8) | 7% |
| 3-HH1OB(2F,3F)-O2 | (3-8) | 9% |
| 3-HEB(2F,3F)B(2F,3F)-O2 | (3-11) | 3% |
| 3-HBB(2F,3CL)-O2 | (3-13) | 4% |
| 1O1-HBBH-5 | (—) | 3% |

NI=81.7° C.; Tc<−20° C.; Δn=0.122; Δ∈=−3.0; Vth=2.30 V; η17.8 mPa·s.

Example 11

| | | |
|---|---|---|
| V-HV2B(2F,3F)-O2 | (1-1) | 6% |
| V-H2VHB(2F,3F)-O2 | (1) | 6% |
| 5-HH-VFF | (2-1) | 3% |
| 4-HH-V | (2-1) | 10% |
| 4-HH-V1 | (2-1) | 8% |
| 5-HB-O2 | (2-2) | 4% |
| 7-HB-1 | (2-2) | 5% |
| 1-BB(F)B-2V | (2-7) | 4% |
| 3-BB(F)B-2V | (2-7) | 4% |
| 3-HHEBH-3 | (2-10) | 3% |
| 3-HHEBH-4 | (2-10) | 3% |
| 3-BB(2F,3F)-O2 | (3-4) | 10% |
| 2O-BB(2F,3F)-O2 | (3-4) | 5% |

| 2-HH1OB(2F,3F)-O2 | (3-8) | 11% |
| 3-HH1OB(2F,3F)-O2 | (3-8) | 18% |

NI=88.4° C.; Tc<−20° C.; Δn=0.112; Δ∈=−3.6; Vth=2.14 V; η=24.0 mPa·s.

The compositions in Example 1 to Example 11 each had a lower minimum temperature in comparison with the composition in Comparative Example 1. Accordingly, the liquid crystal composition according to the invention is concluded to have further excellent characteristics.

Although the invention has been described and illustrated with a certain degree of particularity, it is understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal composition of the invention satisfies at least one of characteristics such as a high maximum temperature, a low minimum temperature, a small viscosity, a suitable optical anisotropy, a large negative dielectric anisotropy, a large specific resistance, a high stability to ultraviolet light, a high stability to heat and a large elastic constant, or has a suitable balance regarding at least two of the characteristics. A liquid crystal display device including such a composition has characteristics such as a short response time, a large voltage holding ratio, a low threshold voltage, a large contrast ratio and a long service life, and thus can be used for a liquid crystal projector, a liquid crystal television and so forth.

What is claimed is:

1. A liquid crystal composition having a negative dielectric anisotropy and contains at least one compound selected from the group of compounds represented by formula (1) as a first component and further containing at least one compound selected from the group of compounds represented by formula (2) as a second component:

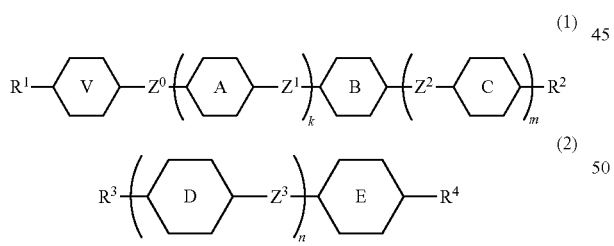

wherein, in formula (1), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine; ring V is 1,4-cyclohexylene or tetrahydropyran-2,5-diyl; ring A and ring C are independently 1,4-cyclohexylene, tetrahydropyran-2,5-diyl, 1,4-phenylene, or 1,4-phenylene in which at least one of hydrogen is replaced by fluorine or chlorine; ring B is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2,6-diyl; $Z^0$, $Z^1$ and $Z^2$ are independently a single bond, ethylene, butene, carbonyloxy or methyleneoxy, wherein, at least one of $Z^0$, $Z^1$ and $Z^2$ is butene; k is 0, 1 or 2; m is 0 or 1; and a sum of k and m is 2 or less;

in formula (2), $R^3$ and $R^4$ are independently alkyl having 1 to 12 carbons, alkenyl having 2 to 12 carbons, alkyl having 1 to 12 carbons in which at least one of hydrogen is replaced by fluorine or chlorine, or alkenyl having 2 to 12 carbons in which at least one of hydrogen is replaced by fluorine or chlorine; ring D and ring E are independently 1,4-cyclohexylene, 1,4-phenylene, 2-fluoro-1,4-phenylene or 2,5-difluoro-1,4-phenylene; $Z^3$ is a single bond, ethylene or carbonyloxy; and n is 1, 2 or 3.

2. The liquid crystal composition according to claim 1, containing at least one compound selected from the group of compounds represented by formula (1-1) to formula (1-3) as the first component:

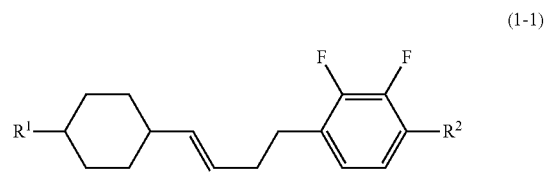

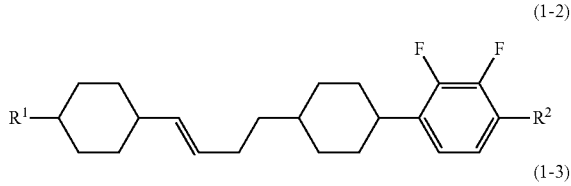

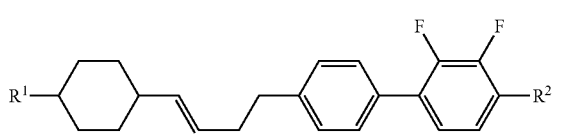

wherein, in formula (1-1) to formula (1-3), $R^1$ and $R^2$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine.

3. The liquid crystal composition according to claim 1, wherein a ratio of the first component is in the range of 3% by weight to 30% by weight based on the weight of the liquid crystal composition.

4. The liquid crystal composition according to claim 1, containing at least one compound selected from the group of compounds represented by formula (2-1) to formula (2-13) as the second component:

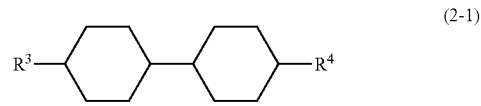

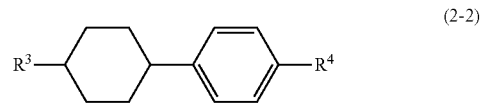

-continued

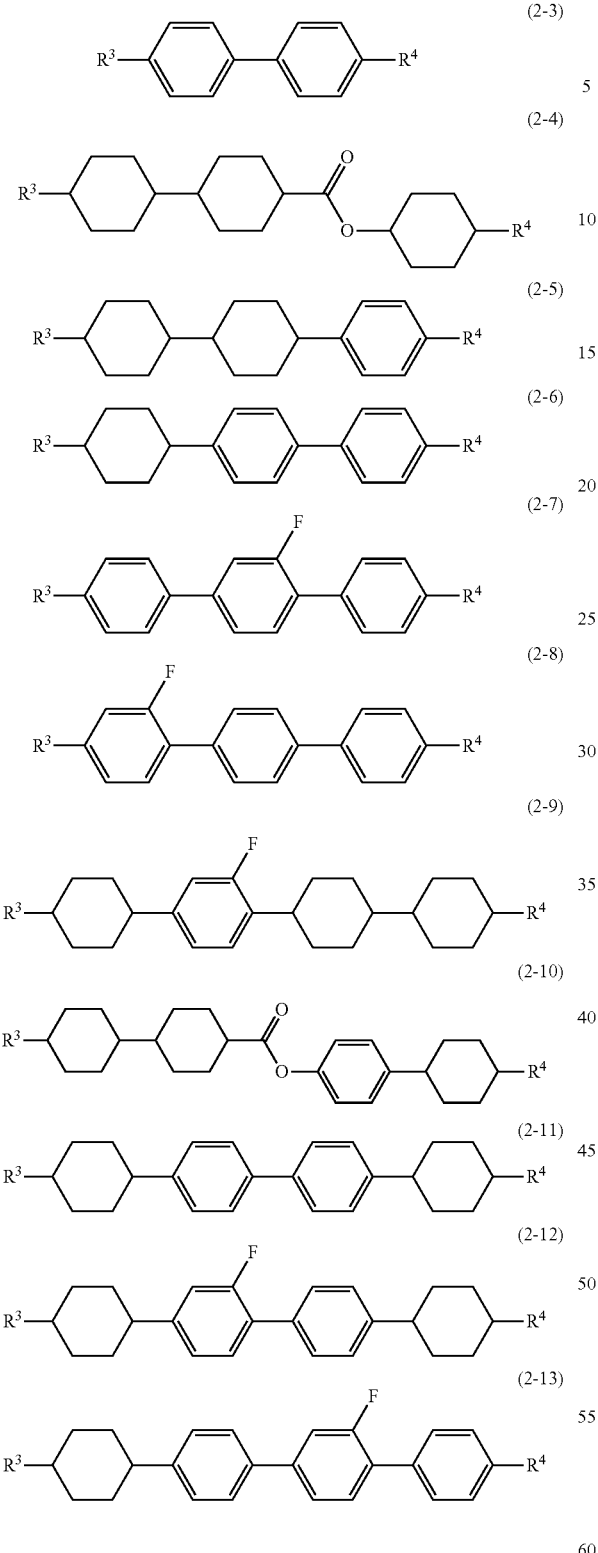

wherein, in formula (2-1) to formula (2-13), $R^3$ and $R^4$ are independently alkyl having 1 to 12 carbons, alkenyl having 2 to 12 carbons, alkyl having 1 to 12 carbons in which at least one of hydrogen is replaced by fluorine or chlorine, or alkenyl having 2 to 12 carbons in which at least one of hydrogen is replaced by fluorine or chlorine.

5. The liquid crystal composition according to claim 1, wherein a ratio of the second component is in the range of 20% by weight to 70% by weight based on the weight of the liquid crystal composition.

6. The liquid crystal composition according to claim 1, containing at least one compound selected from the group of compounds represented by formula (3) as a third component:

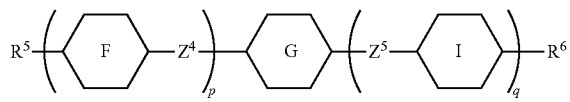

wherein, in formula (3), $R^5$ and $R^6$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine; ring F and ring I are independently 1,4-cyclohexylene, 1,4-cyclohexenylene, tetrahydropyran-2,5-diyl, 1,4-phenylene, or 1,4-phenylene in which at least one of hydrogen is replaced by fluorine or chlorine; ring G is 2,3-difluoro-1,4-phenylene, 2-chloro-3-fluoro-1,4-phenylene, 2,3-difluoro-5-methyl-1,4-phenylene, 3,4,5-trifluoronaphthalene-2,6-diyl or 7,8-difluorochroman-2, 6-diyl;
$Z^4$ and $Z^5$ are independently a single bond, ethylene, carbonyloxy or methyleneoxy; p is 1, 2 or 3; q is 0 or 1; and a sum of p and q is 3 or less.

7. The liquid crystal composition according to claim 6, containing at least one compound selected from the group of compounds represented by formula (3-1) to formula (3-19) as the third component:

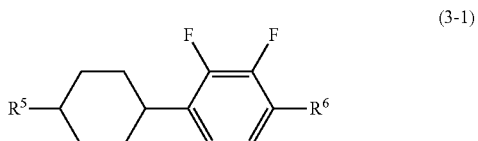

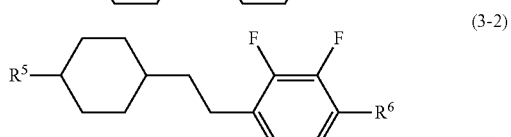

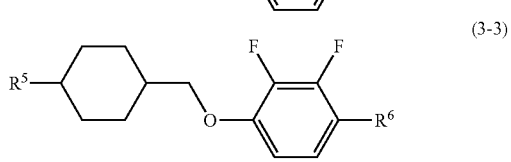

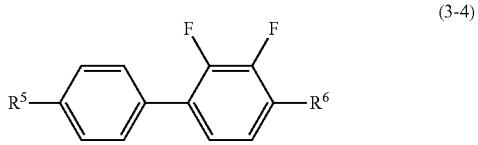

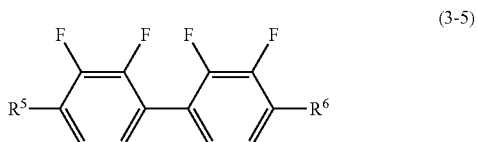

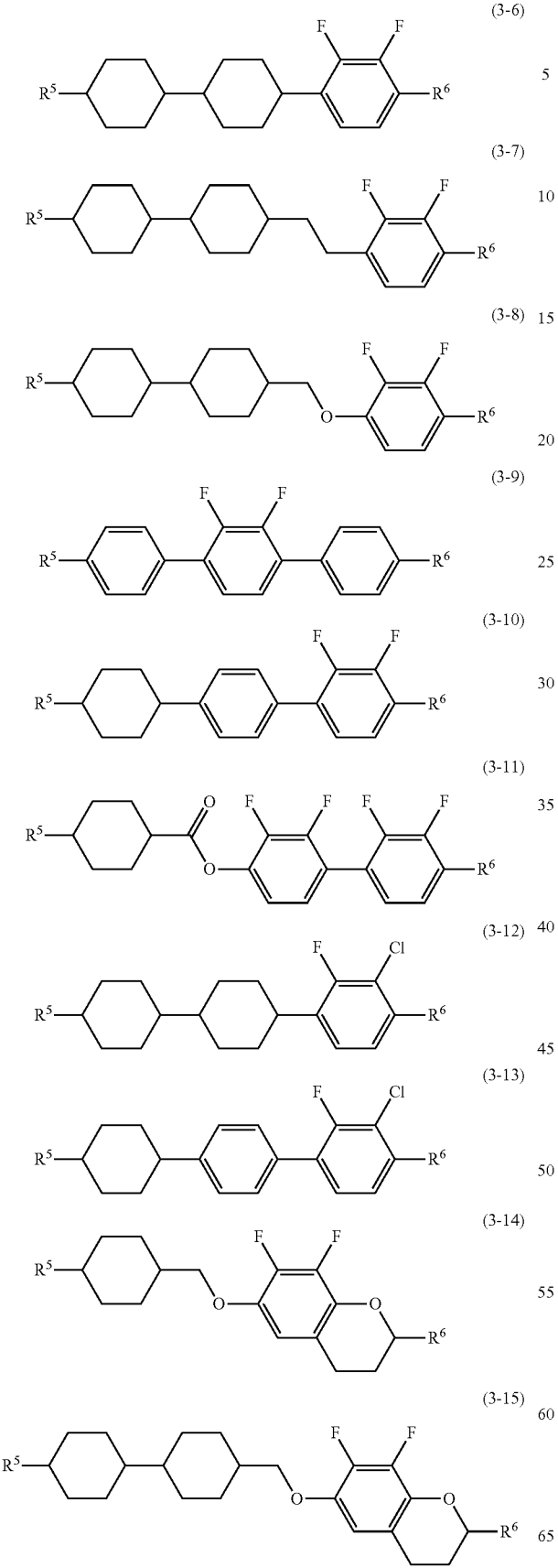
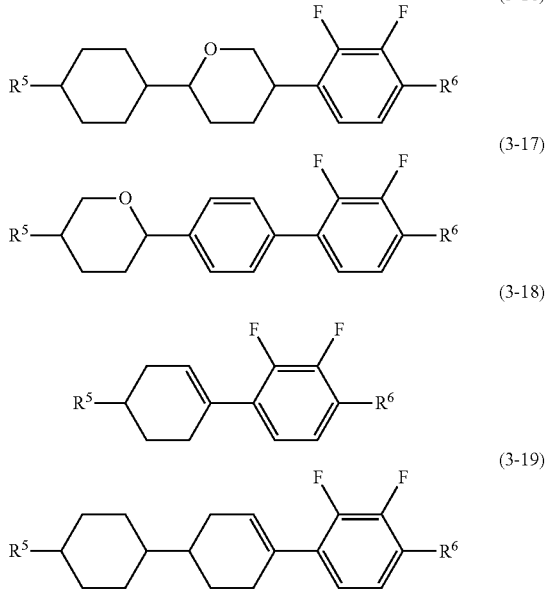

wherein, in formula (3-1) to formula (3-19), $R^5$ and $R^6$ are independently alkyl having 1 to 12 carbons, alkoxy having 1 to 12 carbons, alkenyl having 2 to 12 carbons, alkenyloxy having 2 to 12 carbons, or alkyl having 1 to 12 carbons in which at least one of hydrogen is replaced by fluorine or chlorine.

8. The liquid crystal composition according to claim 6, wherein a ratio of the third component is in the range of 20% by weight to 70% by weight based on the weight of the liquid crystal composition.

9. The liquid crystal composition according to claim 1, containing at least one polymerizable compound selected from the group of compounds represented by formula (4) as an additive component:

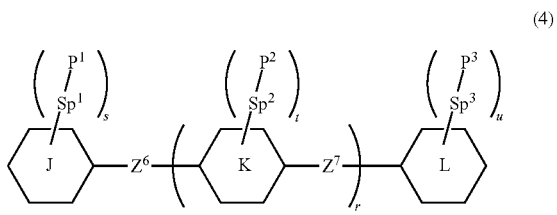

wherein, in formula (4), ring J and ring L are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by fluorine, chlorine, alkyl having 1 to 12 carbons, alkoxy having 1 to 12 carbons, or alkyl having 1 to 12 carbons in which at least one of hydrogen is replaced by fluorine or chlorine; ring K is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by fluorine, chlorine, alkyl having 1 to 12 carbons, alkoxy having 1 to 12 carbons, or alkyl having 1 to 12 carbons in which at least one of hydrogen is replaced by fluorine or chlorine; $Z^6$ and $Z^7$ are independently a single bond or alkylene having 1 to 10 carbons, in the alkylene, at least one of —CH$_2$— may be replaced by —O—, —CO—, —COO— or —OCO—, at least one of —CH$_2$—CH$_2$— may be replaced by —CH=CH—, —C(CH$_3$)=CH—, —CH=C(CH$_3$)— or —C(CH$_3$)=C(CH$_3$)—, and in the groups, at least one of hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one of —CH$_2$— may be replaced by —O—, —COO—, —OCO— or —OCOO—, at least one of —CH$_2$—CH$_2$— may be replaced by —CH=CH— or —C≡C—, and in the groups, at least one of hydrogen may be replaced by fluorine or chlorine; r is 0, 1 or 2; s, t and u are independently 0, 1, 2, 3 or 4; and a sum of s, t and u is 1 or more.

10. The liquid crystal composition according to claim 9, wherein, in formula (4), $P^1$, $P^2$, and $P^3$ are independently a polymerizable group selected from the group of groups represented by formula (P-1) to formula (P-5):

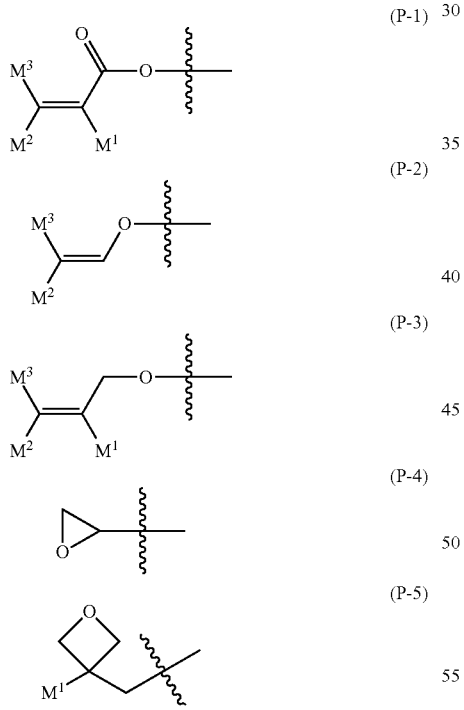

(P-1)

(P-2)

(P-3)

(P-4)

(P-5)

wherein, in formula (P-1) to formula (P-5), $M^1$, $M^2$ and $M^3$ are independently hydrogen, fluorine, alkyl having 1 to 5 carbons, or alkyl having 1 to 5 carbons in which at least one of hydrogen is replaced by fluorine or chlorine.

11. The liquid crystal composition according to claim 9, containing at least one polymerizable compound selected from the group of compounds represented by formula (4-1) to formula (4-27) as the additive component:

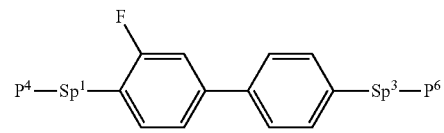

(4-1)

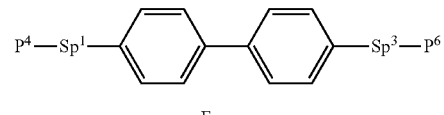

(4-2)

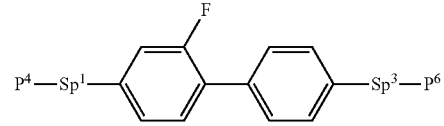

(4-3)

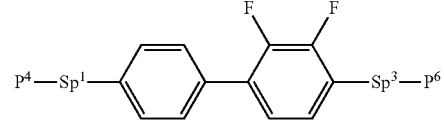

(4-4)

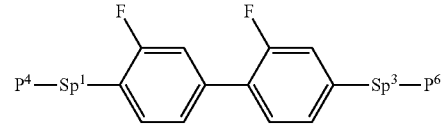

(4-5)

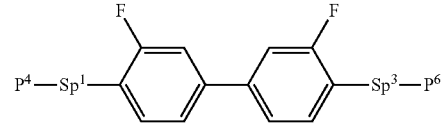

(4-6)

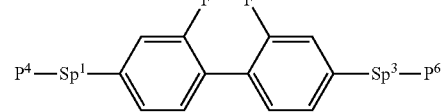

(4-7)

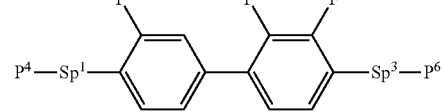

(4-8)

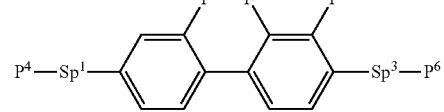

(4-9)

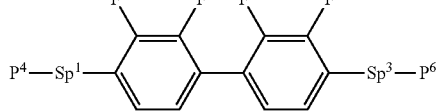

(4-10)

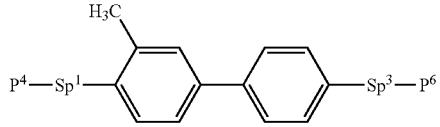

(4-11)

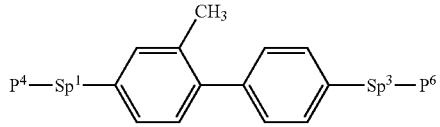

(4-12)

(4-13) 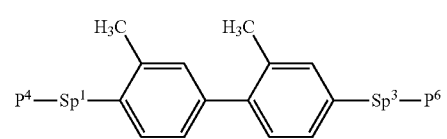
(4-14) 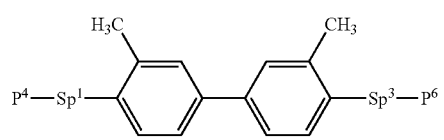
(4-15) 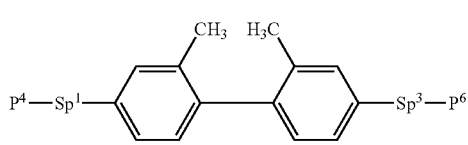
(4-16) 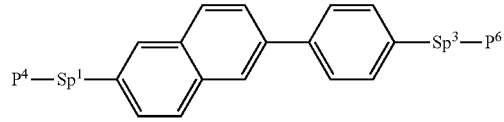
(4-17) 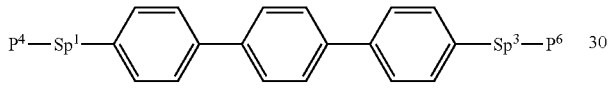
(4-18) 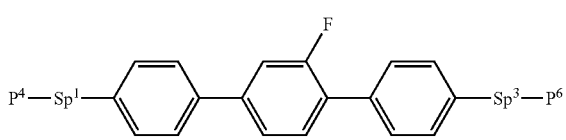
(4-19) 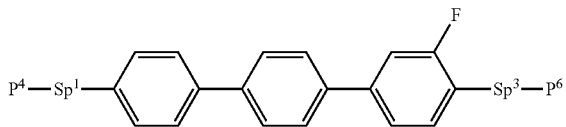
(4-20) 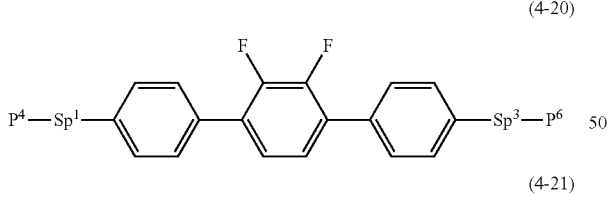
(4-21) 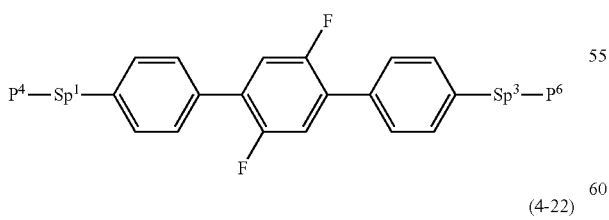
(4-22) 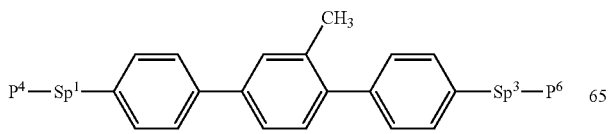
(4-23) 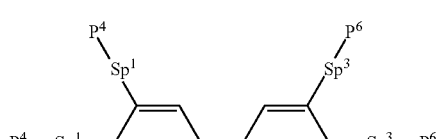
(4-24) 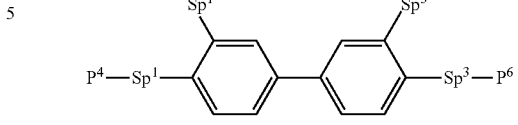
(4-25) 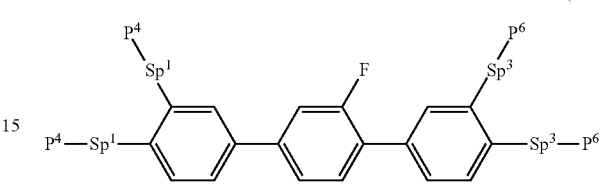
(4-26) 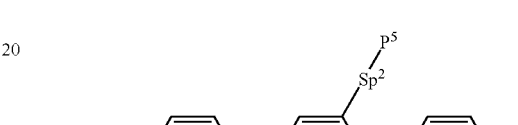
(4-27) 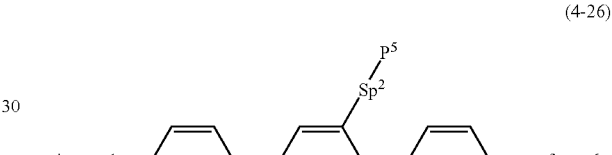
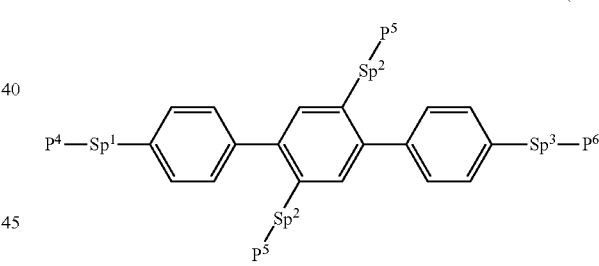
wherein, in formula (4-1) to formula (4-27), $P^4$, $P^5$ and $P^6$ are independently a polymerizable group selected from the group of groups represented by formula (P-1) to formula (P-3);
(P-1) 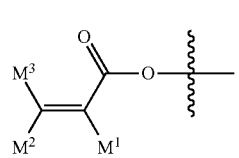
(P-2) 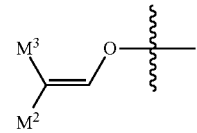

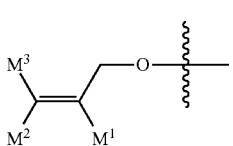
(P-3)

wherein, in formula (P-1) to formula (P-3), $M^1$, $M^2$ and $M^3$ are independently hydrogen, fluorine, alkyl having 1 to 5 carbons, or alkyl having 1 to 5 carbons in which at least one of hydrogen is replaced by fluorine or chlorine; and in formula (4-1) to formula (4-27), Sp, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine.

12. The liquid crystal composition according to claim 9, wherein a ratio of addition of the additive component is in the range of 0.03% by weight to 10% by weight based on the weight of the liquid crystal composition.

13. The liquid crystal composition according to claim 6, containing at least one polymerizable compound selected from the group of compounds represented by formula (4) as an additive component:

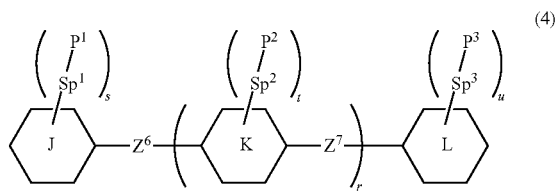
(4)

wherein, in formula (4), ring J and ring L are independently cyclohexyl, cyclohexenyl, phenyl, 1-naphthyl, 2-naphthyl, tetrahydropyran-2-yl, 1,3-dioxane-2-yl, pyrimidine-2-yl or pyridine-2-yl, and in the rings, at least one of hydrogen may be replaced by fluorine, chlorine, alkyl having 1 to 12 carbons, alkoxy having 1 to 12 carbons, or alkyl having 1 to 12 carbons in which at least one of hydrogen is replaced by fluorine or chlorine; ring K is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, tetrahydropyran-2,5-diyl, 1,3-dioxane-2,5-diyl, pyrimidine-2,5-diyl or pyridine-2,5-diyl, and in the rings, at least one of hydrogen may be replaced by fluorine, chlorine, alkyl having 1 to 12 carbons, alkoxy having 1 to 12 carbons, or alkyl having 1 to 12 carbons in which at least one of hydrogen is replaced by fluorine or chlorine; $Z^6$ and $Z^7$ are independently a single bond or alkylene having 1 to 10 carbons, in the alkylene, at least one of —$CH_2$— may be replaced by —O—, —CO—, —COO— or —OCO—, at least one of —$CH_2$—$CH_2$— may be replaced by —CH=CH—, —C($CH_3$)=CH—, —CH=C($CH_3$)— or —C($CH_3$)=C($CH_3$)—, and in the groups, at least one of hydrogen may be replaced by fluorine or chlorine; $P^1$, $P^2$ and $P^3$ are independently a polymerizable group; $Sp^1$, $Sp^2$ and $Sp^3$ are independently a single bond or alkylene having 1 to 10 carbons, and in the alkylene, at least one of —$CH_2$— may be replaced by —O—, —COO—, —OCO— or —OCOO—, at least one of —$CH_2$—$CH_2$— may be replaced by —CH=CH— or —C≡C—, and in the groups, at least one of hydrogen may be replaced by fluorine or chlorine; r is 0, 1 or 2; s, t and u are independently 0, 1, 2, 3 or 4; and a sum of s, t and u is 1 or more.

14. A liquid crystal display device, including the liquid crystal composition according to claim 1.

15. The liquid crystal display device according to claim 14, wherein an operating mode of the liquid crystal display is an IPS mode, a VA mode, an FFS mode or an FPA mode, and a driving mode of the liquid crystal display device is an active matrix mode.

16. A polymer sustained alignment mode liquid crystal display device, wherein the device includes the liquid crystal composition according to claim 9, or a polymerizable compound in the liquid crystal composition is polymerized.

* * * * *